United States Patent [19]
Habberfield et al.

[11] Patent Number: 5,574,018
[45] Date of Patent: Nov. 12, 1996

[54] CONJUGATES OF VITAMIN B12 AND PROTEINS

[75] Inventors: Alan D. Habberfield, Pacific Palisades; Olaf B. Kinstler; Colin G. Pitt, both of Thousand Oaks, all of Calif.

[73] Assignee: Amgen Inc., Thousand Oaks, Calif.

[21] Appl. No.: 282,384

[22] Filed: Jul. 29, 1994

[51] Int. Cl.[6] .......................... A61K 31/68; A61K 38/41; C07H 23/00; C07K 14/00
[52] U.S. Cl. ............................. 514/21; 424/851; 424/854; 514/8; 514/12; 530/351; 530/395; 530/399; 530/409
[58] Field of Search .................................. 424/85.1, 85.4; 514/8, 12, 21; 530/351, 395, 399, 409; 536/26.4, 26.41, 26.44

[56] References Cited

U.S. PATENT DOCUMENTS

| | | | |
|---|---|---|---|
| 3,981,863 | 9/1976 | Niswender et al. | 536/25 |
| 5,428,023 | 6/1995 | Russell-Jones et al. | 514/21 |

FOREIGN PATENT DOCUMENTS

| | | |
|---|---|---|
| 0220030A3 | 4/1987 | European Pat. Off. . |
| W087/02251 | 4/1987 | WIPO . |
| W090/12095 | 10/1990 | WIPO . |
| W092/17167 | 10/1992 | WIPO . |
| W094/27613 | 12/1994 | WIPO . |
| W094/27641 | 12/1994 | WIPO . |
| W094/28015 | 12/1994 | WIPO . |

OTHER PUBLICATIONS

Marques et al., Inorganica Chimica Acta, 162 (1989) 151–155.
Nexo, Biochimica et Biophysica Acta, 379 (1975) 189–192.
Yamada et al., Journal of Biol. Chem., 247 (1972) No. 19, 6266–6270.
Chow et al., Am. Journ. Clin. Nutr., 6 (1958) No. 1, 30–33.
Olesen et al., Biochimica et Biophysica Acta, 243 (1971) 66–74.
Bioconjugate Chem., vol. 6, No. 4, pp. 459–465 (1995).

*Primary Examiner*—Ponnathapura Achutamurthy
*Attorney, Agent, or Firm*—Richard J. Mazza

[57] ABSTRACT

Therapeutically useful proteins are conjugated to vitamin $B_{12}$ by covalent binding at the primary hydroxyl site of the ribose moiety. The resulting conjugates are biologically active and can be formulated into pharmaceutical compositions suitable for delivery by various routes of administration, preferably oral. Uptake in the gut following oral delivery is further enhanced by the co-administration of purified intrinsic factor.

24 Claims, 13 Drawing Sheets

1. R=H
2. R=CO-CH$_2$CH$_2$CH$_2$-COR$_1$
   R$_1$=OH or protein
3. R=CO-CH$_2$CH$_2$CH$_2$-COR$_2$
   R$_2$=N-hydroxysuccinimidyl
4. R=CO-CH$_2$CH$_2$CH$_2$-CONH-(CH$_2$)$_{12}$-NH$_2$
5. R=CO-CH$_2$CH$_2$CH$_2$-CONH-(CH$_2$)$_{12}$-NHCOCH$_2$CH$_2$-S-R$_3$
   R$_3$=2-thiopyridyl or protein
6. R=CO-CH$_2$CH$_2$CH$_2$-CONH-(CH$_2$)$_7$COR$_1$
   R$_1$=OH or protein
7. R=CO-CH$_2$CH$_2$CH$_2$-CONH-(CH$_2$)$_7$COR$_2$
   R$_2$=N-hydroxysuccinimidyl
8. R=CO-CH$_2$CH$_2$CH$_2$-CONHNHCO(CH$_2$)$_4$CONHNH R$_1$
   R$_1$=H or protein
8A. R=CO-CH$_2$CH$_2$CH$_2$-CONHNHCO(CH$_2$)$_4$CONHN=R$_4$
   R$_4$= protein $R_2$= -O-N(succinimidyl)

$R_3$= -S-(2-pyridyl)

FIG. 1

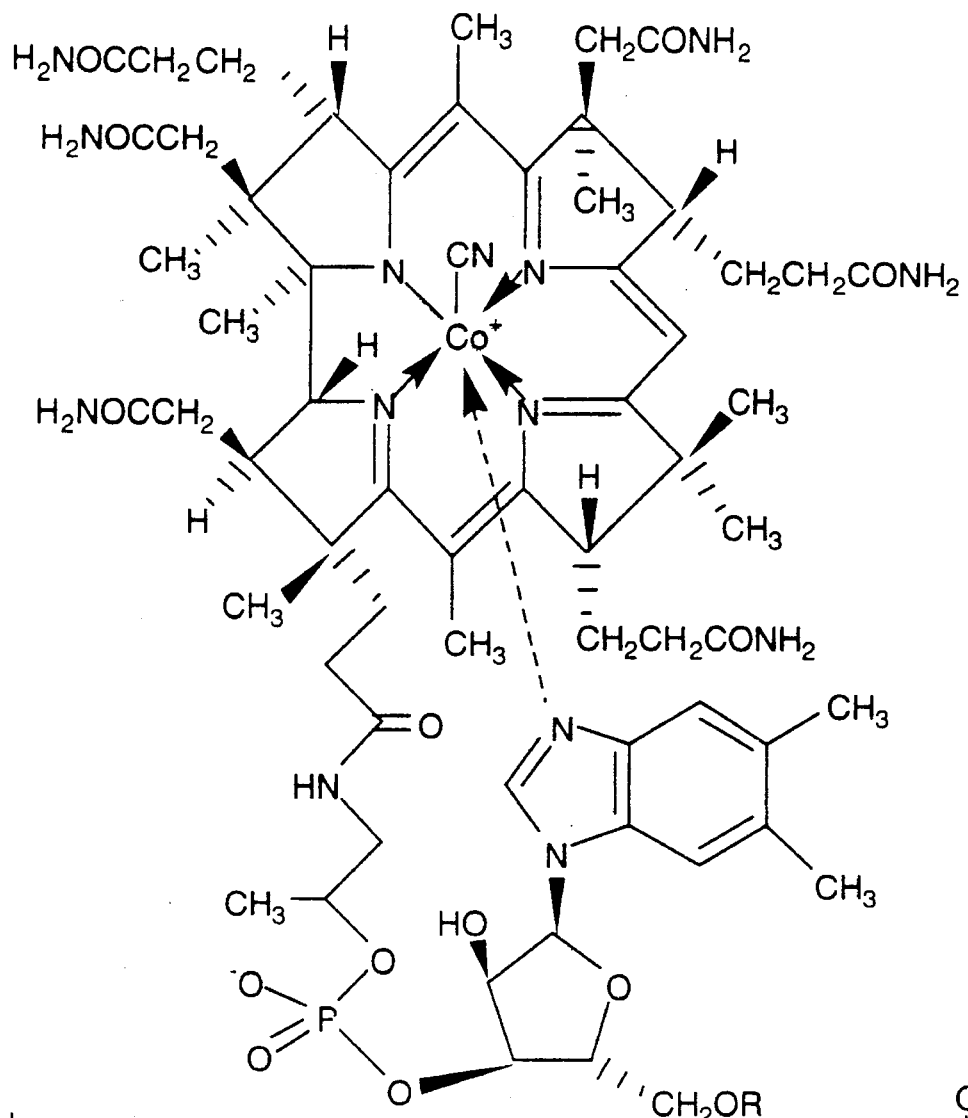

1. R=H
2. R=CO-CH$_2$CH$_2$CH$_2$-COR$_1$
   R$_1$=OH or protein
3. R=CO-CH$_2$CH$_2$CH$_2$-COR$_2$
   R$_2$=N-hydroxysuccinimidyl
4. R=CO-CH$_2$CH$_2$CH$_2$-CONH-(CH$_2$)$_{12}$-NH$_2$
5. R=CO-CH$_2$CH$_2$CH$_2$-CONH-(CH$_2$)$_{12}$-NHCOCH$_2$CH$_2$-S-R$_3$
   R$_3$=2-thiopyridyl or protein
6. R=CO-CH$_2$CH$_2$CH$_2$-CONH-(CH$_2$)$_7$COR$_1$
   R$_1$=OH or protein
7. R=CO-CH$_2$CH$_2$CH$_2$-CONH-(CH$_2$)$_7$COR$_2$
   R$_2$=N-hydroxysuccinimidyl
8. R=CO-CH$_2$CH$_2$CH$_2$-CONHNHCO(CH$_2$)$_4$CONHNH R$_1$
   R$_1$=H or protein
8A. R=CO-CH$_2$CH$_2$CH$_2$-CONHNHCO(CH$_2$)$_4$CONHN=R$_4$
    R$_4$= protein

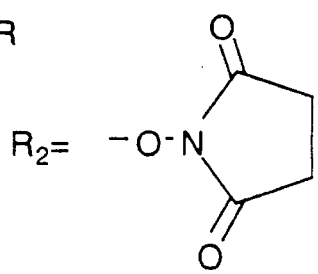

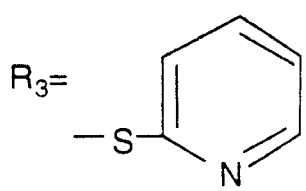

FIG. 3

$B_{12}OC(O)(CH_2)_3CO-R_1$
$(2, R_1 = EPO)$
EXAMPLE 3

$B_{12}OC(O)(CH_2)_3CO-R_2$
$(3, R_2 = N\text{-hydroxysuccinimidyl})$ $B_{12}OC(O)(CH_2)_3CONH(CH_2)_7CO-R_1$
$(6, R_1 = EPO)$
EXAMPLE 11

$B_{12}OC(O)(CH_2)_3CONH(CH_2)_7CO-R_2$
$(7, R_2 = N\text{-hydroxysuccinimidyl})$ 1. $NaIO_4$
2. $B_{12}OC(O)(CH_2)_3CONHNHCO(CH_2)_4CONHNH-R_1$
$(8, R_1 = H)$ $B_{12}OC(O)(CH_2)_3CONHNHCO(CH_2)_4CONHNH=R_4$
$(8A, R_4 = EPO)$
EXAMPLE 13

EPO $EDC/B_{12}OC(O)(CH_2)_3CONHNHCO(CH_2)_4CONHNH-R_1$
$(8, R_1 = H)$ $B_{12}OC(O)(CH_2)_3CONHNHCO(CH_2)_4CONHNH-R_1$
$(8, R_1 = EPO)$
EXAMPLE 15

FIG. 4

$B_{12}OC(O)(CH_2)_3CO\text{-}NH(CH_2)_{12}NH\text{-}C(O)CH_2\text{-}S\text{-}R_3$
(5, $R_3$=GCSF)
EXAMPLE 7

↑

$B_{12}OC(O)(CH_2)_3CO\text{-}NH(CH_2)_{12}NH\text{-}C(O)CH_2\text{-}S\text{-}R_3$
(5, $R_3$=2-thiopyridyl)

G-CSF $B_{12}OC(O)(CH_2)_3CO\text{-}NH(CH_2)_7COR_2$
(7, $R_2$=N-hydroxysuccinimidyl)

→

$B_{12}OC(O)(CH_2)_3CO\text{-}NH(CH_2)_7COR_1$
(6, $R_1$=GCSF)
EXAMPLE 10

$B_{12}OC(O)\text{-}(CH_2)_3\text{-}COR_1$
(2, $R_1$=GCSF)
EXAMPLE 2

↖

$B_{12}OC(O)\text{-}(CH_2)_3\text{-}COR_2$
(3, $R_2$=N-hydroxysuccinimidyl)

EXAMPLE 8

CONJUGATES OF VITAMIN B12 AND PROTEINS

FIELD OF THE INVENTION

This invention relates to biologically active conjugates of vitamin $B_{12}$ and therapeutic proteins which can be delivered by various routes of administration, including orally, to achieve therapeutically effective levels of the protein in the body.

BACKGROUND OF THE INVENTION

The gastrointestine (i.e., G.I.) is an organ of the body that functions to physically, chemically and enzymatically process and break down ingested nutrients. The G.I. tract is also responsible for the uptake of nutrients into the body and the elimination of waste products. The G.I. tract consists of the stomach, which digests nutrients, stimulates other regions of the G.I. tract to secrete digestive enzymes, stores food temporarily, and releases chyme into the intestine at a controlled rate. The stomach also serves to secrete numerous chemicals and biological factors. However, the uptake of nutrients is not a significant function. Distal to the stomach is the duodenum, where neutralization of acidic chyme occurs. Surfactants, for the digestion of lipids, and proteases, for the degradation of proteins, are also secreted into the duodenum. As with the stomach, there is little absorption of nutrients in the duodenum. Uptake of nutrients, or more specifically their digestive products, takes place principally in the small intestine, comprising the jejunum and the ileum. On the other hand, the large intestine, consisting of the cecum the colon, are responsible for the storage of waste and water, and also for salt balance. There is little enzymatic activity in the large intestine, which is the least permeable section of the G.I. tract.

The majority of the surface area in the small and large intestines is made up of a layer of epithelial cells called enterocytes, which are specialized villus absorptive cells. The intestine is also lined with a mucus layer; Clamp, J. R., in *Food Allergy* and *Intolerance*, edited by J. Brostoff and S. J. Challacombe, pages 190–205 (1987). The mucus layer acts as a barrier to macromolecules, e.g., molecules having a molecular weight of greater than 17 kilodaltons; Thomson, A. B. R. and Dietschy, J. M. in *Pharmacology of the Intestinal* Permeation II, edited by T. Z. Czaky, page 20 (1984). The enterocyte layer, on the other hand, forms a tight lipid barrier to smaller molecules, i.e., peptides of about 500 daltons or so; Smith, P. L. et al., Volume 8, pages 253–290 (1992). Thus, the lining of the intestine serves as an efficient barrier to both lipophilic and hydrophilic molecules. As a consequence, the oral administration of a large, macromolecular therapeutic such as a protein is normally limited as to effectiveness.

However, some molecules are specifically taken up in the G.I. tract as a normal function of the digestive process. These substances include amino acids, glucose and vitamins, among others. For such molecules, native biological mechanisms for transportation across the intestinal lining exist. In particular, amino acids and glucose are taken up by transporter molecules located in the lumenal or apical membrane domain of enterocytes. Receptors for vitamin uptake are also present in the apical domain of the enterocyte lining.

Of special interest here is the biological mechanism for the uptake of vitamin $B_{12}$ ("$VB_{12}$"). $VB_{12}$, also known as cyanocobalamin, is composed of a corrin ring structure which surrounds an atom of cobalt. $VB_{12}$ is normally ingested through animal products and released into the acidic environment of the stomach. A transport protein for $VB_{12}$, called intrinsic factor ("IF"), is also secreted into the lumen of the stomach in humans by parietal cells; Levine, J. S. et al., *Gastroenterology*, Volume 79, pages 493–502 (1980). IF, a glycoprotein of about 44 kilodaltons, is typically released in amounts far in excess of those needed to promote the physiological absorption of $VB_{12}$. Once secreted, IF binds to $VB_{12}$ with high affinity ($K_a$ 1.9× $10^{12}M^{-1}$), but only under the neutral conditions of pH present in the duodenum. After IF becomes complexed with $VB_{12}$ it becomes resistant to the proteases present in that organ which degrade most proteins; Allen, R. H. et al., *Journal of Clinical Investigation*, Volume 61, pages 47–54 (1978).

Receptors that bind to the IF-$VB_{12}$ complex are present in the apical membrane domain of enterocytes, predominantly in the ileum; Hagedorn, C. H. and Alpers, D. H., *Gastroenterology*, Volume 73, pages 1019–1022(1977). While the number of receptors for the IF-$VB_{12}$ complex on each enterocyte is small, i.e., about 300–400 per cell, the binding affinity for the IF-$VB_{12}$ complex is high, $4.0 \times 10^9$ $M^{-1}$; Mathan, V. I. et al., *Journal of Clinical Investigation*, Volume 54, pages 598–608 (1974). After binding to its receptor, the IF-$VB_{12}$ complex is internalized in the enterocyte cell body; Kapadia, C. R. and Donaldson, R. M., *Gastroenterology*, Volume 76, page 1163P (1979). IF is apparently then degraded in the enterocyte. $VB_{12}$, on the other hand, is trancytosed across the cell and then, in a complex with the serum transporting protein, transcobalamin II (TCII), is released into the systemic circulation; Rothenberg, S. P. et al., *British Journal of Haemotology*, Volume 40, page 401 (1978), and Dix, C. J. et al., *Gastroenterology*, Volume 98, pages 1272–1279 (1990).

It has been proposed that this $VB_{12}$ uptake mechanism may be utilized to transport biologically active substances such as drugs, hormones, antigenic material, and the like, from the intestinal lumen into circulatory blood by covalently coupling these substances to $VB_{12}$. Published European patent application 0 220 030 A2 discloses a process for the preparation of $VB_{12}$-polypeptide conjugates involving the acid hydrolysis of amide groups on the propionamide side chains adjacent to rings A, B and C of $VB_{12}$, followed by chemical linking to amino groups of the polypeptide through the use of a carbodiimide. The synthesis of conjugates of $VB_{12}$ with bovine serum albumin (BSA), neomycin sulfate and a D-lys-6 analog of lutenizing hormone releasing hormone (LHRH) is exemplified in the application. In addition, the oral administration of $VB_{12}$-BSA and $VB_{12}$-lys-6-LHRH conjugates to mice is demonstrated. See, also, Marques et al., *Inorganica Chimica Acta*, Volume 162, pages 151–155 (1989).

SUMMARY OF THE INVENTION

This invention provides biologically active conjugates of vitamin $B_{12}$ and a therapeutically useful protein which are useful to treat mammalian species. Specifically, these conjugates are formed using a chemical approach involving covalently linking $VB_{12}$ to the therapeutic protein via the primary (5') hydroxyl group of the ribose moiety of $VB_{12}$. The resulting conjugates are capable of administration to mammals through various modes of delivery, preferably oral. In particular, when delivered orally the conjugates of this invention bind to intrinsic factor (IF), in the gastrointestinal tract of a vertebrate host. Once the $VB_{12}$-protein conjugate has bound to IF it is taken up by the enterocytes and transported into the bloodstream, retaining the biological activity of the protein therapeutic. For oral administration, the conjugates are preferably used together with purified intrinsic factor (IF) transporter protein, which results in further increases in the absorption.

In general, biologically active conjugates of this invention may be prepared by reacting the therapeutically active protein with 5'-O-[glutaroyl]cyanocobalamin under conditions which form covalent bonds between the two. Preferably, a 5'-O-glutaroyl derivative of $VB_{12}$ is formed by acylation of $VB_{12}$ with a reactive glutaric acid derivative, for example, the anhydride, to selectively convert the primary hydroxyl group (5'-OH) on the α-ribose moiety to a chemically reactive carboxyl group. The $VB_{12}$ derivative thus obtained is then preferably reacted with a functional linker and/or spacer group to form a second derivative, which in turn is reacted with the therapeutic protein to form a biologically active conjugate.

In addition to these conjugates and the method for their preparation just described, this invention also includes pharmaceutical compositions containing the conjugates. Such compositions may, but need not, also include absorption enhancing amounts of intrinsic factor, which may be a naturally occurring or recombinant exogenous form.

The invention encompasses the use of a variety of therapeutic proteins, preferably, granulocyte colony stimulating factor (G-CSF), erythropoietin (EPO) or consensus interferon (IFN-Con), the uses of which are illustrated in the detailed description of the invention which follows further below.

For purposes of this disclosure, the terms "$VB_{12}$" and "cyanocobalamin" are used interchangeably to mean the same substance.

BRIEF DESCRIPTION OF THE DRAWINGS

FIG. 1 is a three-dimensional illustration of the chemical structure of derivatives of $VB_{12}$, including intermediates as well as $VB_{12}$-protein conjugate end products in accordance with this invention.

FIG. 3 is a schematic diagram of methods for the preparation of conjugates of $VB_{12}$ and EPO in accordance with the invention.

FIG. 4 is a schematic diagram of methods for the preparation of conjugates of $VB_{12}$ and G-CSF in accordance with the invention.

DETAILED DESCRIPTION OF THE INVENTION

Figure 2:
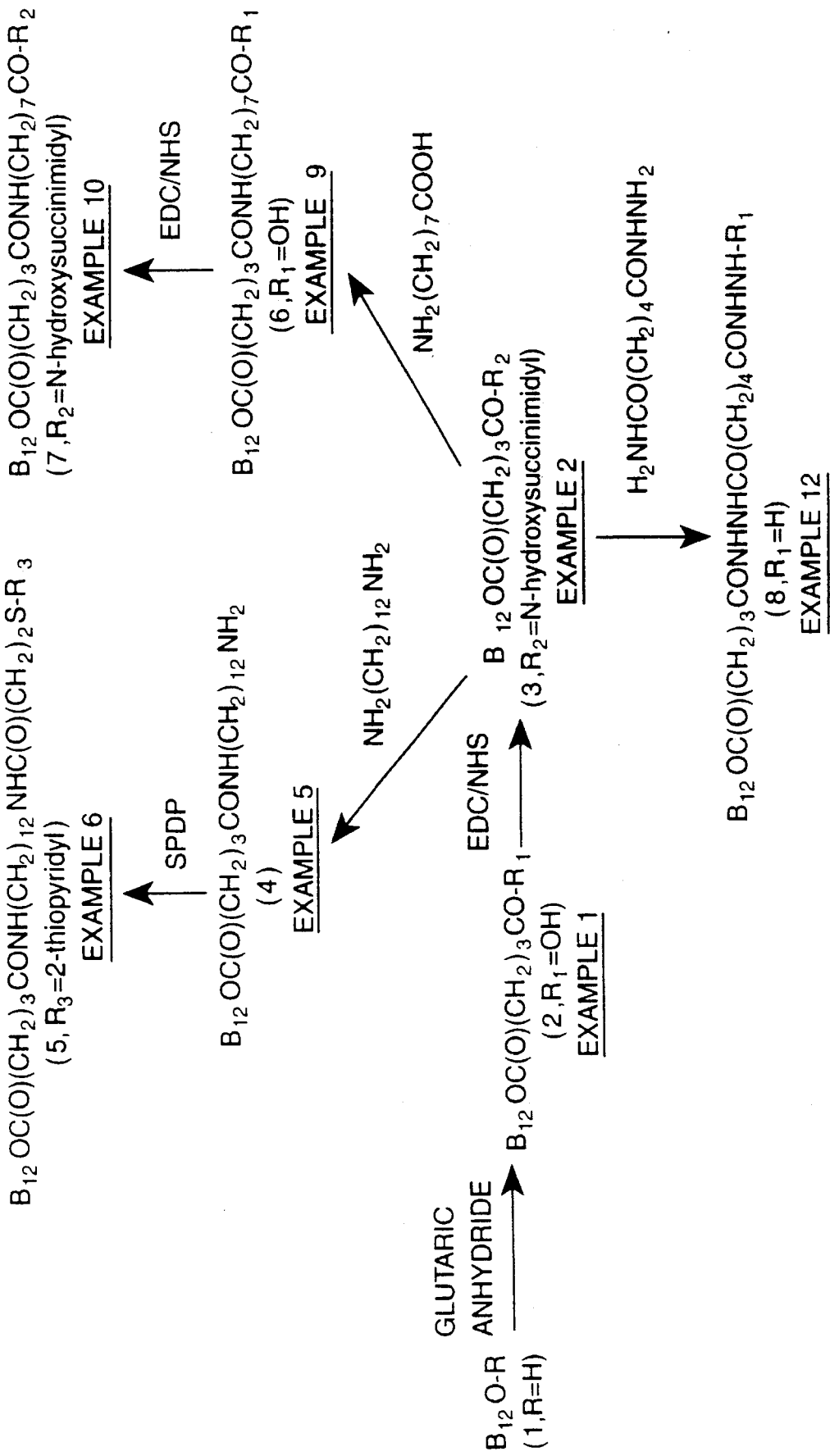
FIG. 2 is a schematic diagram of methods for the preparation of derivatives of $VB_{12}$, these derivatives being useful to form $VB_{12}$-protein conjugates in accordance with the invention. The numbers (1,2,3, etc. preceding the substituent designations ($R_1$, $R_2$, $R_3$, etc.) in this Figure as well as in FIGS. 3–6 relate back to those numbers listed under the formula in FIG. 1.
Figure 5:
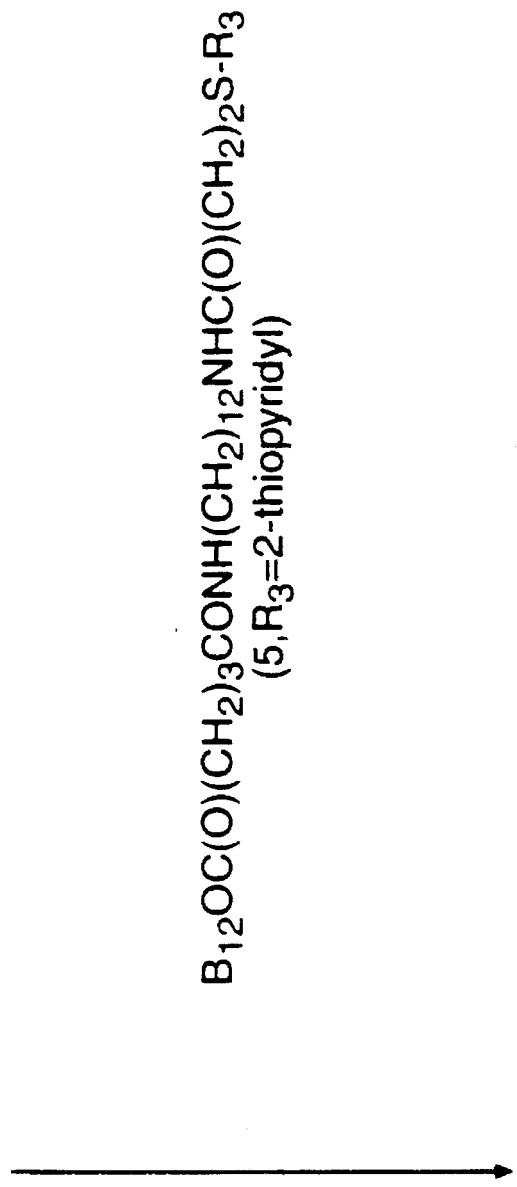
FIG. 5 is a schematic diagram of methods for the preparation of conjugates of $VB_{12}$ and pegylated (polyethylene glycol modified) G-CSF in accordance with the invention.
Figure 6:
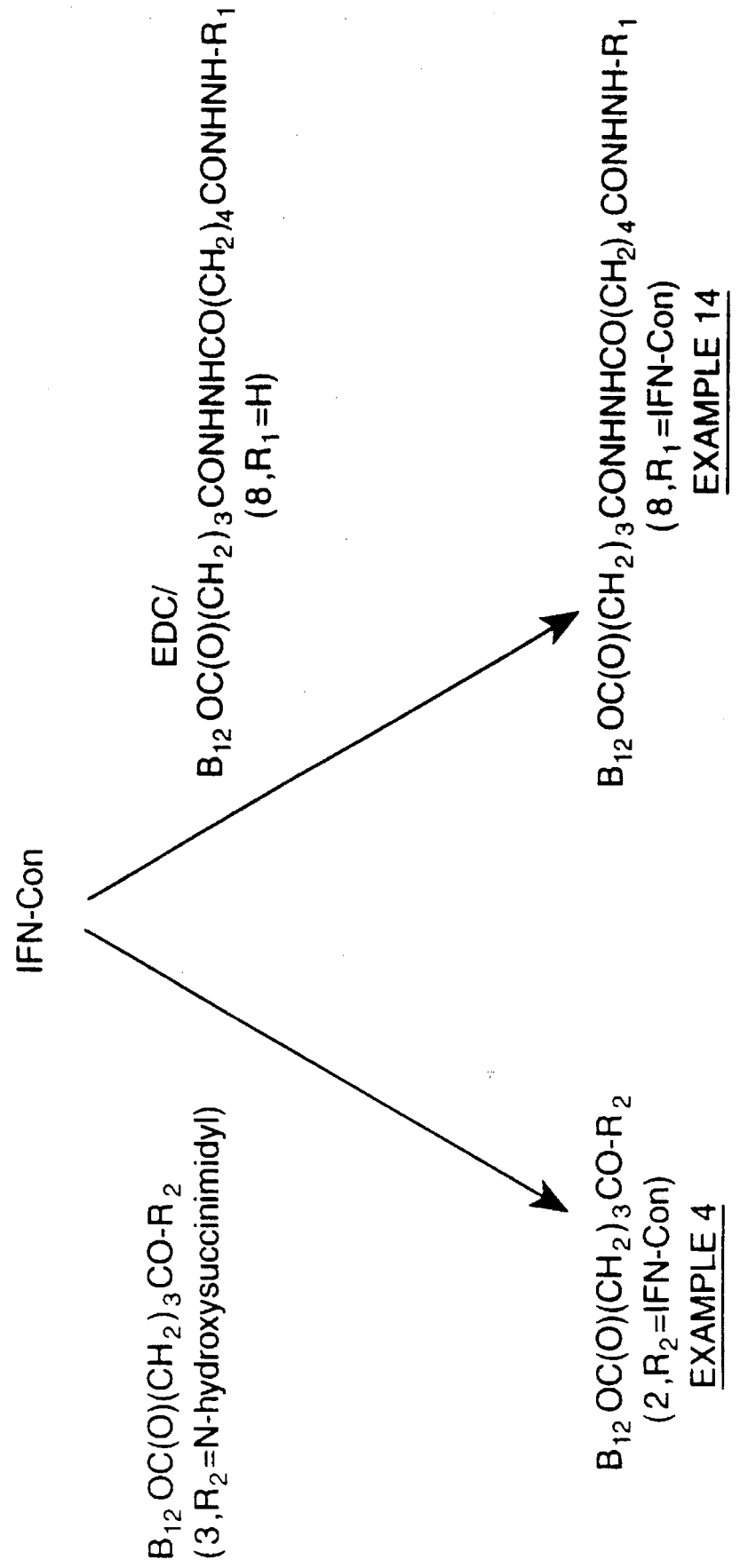
FIG. 6 is a schematic diagram of methods for the preparation of conjugates of $VB_{12}$ and IFN-Con in accordance with the invention.

Preferably, conjugates of $VB_{12}$ and protein according to this invention will be of the formula:

in which R is (1) CO—$(CH_2)_n$—$COR_1$ wherein $R_1$ is the protein, or (2) CO—$(CH_2)_n$—CONH—$(CH_2)_{12}$—NHCOCH$_2$CH$_2$—S—$R_3$ wherein $R_3$ is the protein, or (3) CO—$(CH_2)_n$—CONH—$(CH_2)_7COR_1$ wherein $R_1$ is the protein, or (4) CO—$(CH_2)_n$—CONHNHCO$(CH_2)_4$ CONHNHR$_1$ wherein $R_1$ is the protein, or (5) CO—$(CH_2)_n$—CONHNHCO$(CH_2)_4$ CONHN=$R_4$ wherein $R_4$ is the protein, and n is an integer from 1 to 12.

In the most preferred embodiments, such conjugates will be in accordance with the formula of FIG. 1.

Any polypeptide which is a therapeutically useful protein and is capable of covalent binding to the VB$_{12}$ compound can be utilized in the practice of this invention. The protein can be, for instance, either recombinant or naturally occurring and can include, but is not limited to, cytokines such as granulocyte colony stimulating factor (G-CSF), epidermal growth factor (EGF), erythropoietin (EPO), interferons, such as alpha, beta, gamma, etc., granulocyte/macrophage colony stimulating factor (GM-CSF), keratinocyte growth factor (KGF), the interleukins, such as IL-1, IL-2, etc., among others. Also encompassed are neurotrophic factors such as nerve growth factor (NGF), brain-derived neurotrophic factor (BDNF), neurotrophin-3 (NT-3), and the like. Once conjugated with VB$_{12}$ in accordance with this invention, the protein can be expected to be useful for the same therapautic purposes as if unconjugated.

The invention is illustrated further below with respect to granulocyte colony stimulating factor (G-CSF), erythropoietin (EPO) and consensus interferon (IFN-Con), in particular, which are preferred materials for the practice of this invention. These proteins are known to be useful therapeutically for the treatment of specific diseases or disorders. G-CSF is approved for use in the treatment of neutropenia (i.e., neutrophil deficiency) in patients undergoing chemotherapy for cancer. EPO is approved for use in the treatment of chronic anemia in patients undergoing kidney dialysis. IFN-Con is in human clinical trials for the treatment of viral hepatitis infections.

Methods for the recombinant production and purification of EPO are described in U.S. Pat. No. 4,703,008 (Lin), G-CSF are described in U.S. Pat. Nos. 4,810,643 (Souza), and 4,999,291 (Souza), and IFN-Con are described in U.S. Pat. Nos. 4,897,471 (Stabinsky) and 4,695,623 (Stabinsky), the disclosures of which are incorporated herein by reference.

Also contemplated are proteins, such as the above mentioned and others, to which polymers such as polyethylene glycol have been covalently attached to influence biological properties; see, for example, U.S. Pat. No. 4,179,337 (Davis), the disclosure of which is incorporated herein by reference. Other potential carriers for use with the protein include polymer-based microparticles, liposomes and proteinoids, to name some.

Conjugates of VB$_{12}$ and a therapeutic protein in accordance with this invention are obtained by a method which preferably comprises obtaining a 5'-O-glutaroyl derivative of VB$_{12}$ by acylation of the 5'-OH group on the ribose moiety. Chemical modification of the 5'-O-glutaroyl derivative is achieved by providing at least one functional group capable of forming a chemical linkage, and reacting the modified 5'-O-glutaroyl derivative with the therapeutic protein under conditions which form the conjugate.

Typically, the acylation step will be carried out by dissolving VB$_{12}$ in a suitable solvent, such as dimethylsulfoxide, treating the VB$_{12}$ solution with a suitable reactive glutaric acid derivative (such as anhydride), and isolating the target compound, namely 5'-O-glutaroyl-VB$_{12}$, by ion exchange chromatography in 60–70% yields. This route of preparation of the VB$_{12}$ carboxylic acid derivative with a preserved ability to bind to IF has advantages over known cyanocobalamin propionamide side chain hydrolysis approaches in which the only suitable monoacid, namely the e-monocarboxylic acid, is obtained in only 9–10% yields. The VB$_{12}$ carboxylic acid derivative thus obtained can be conjugated to a protein directly (in the presence of a suitable crosslinking reagent) or derivatized further to form a second derivative suitable for conjugation with the protein.

In general, this invention provides a method for the production of VB$_{12}$-protein conjugates comprising at least one VB$_{12}$ molecule per protein molecule by a process comprising the following steps:

a) Converting the 5'-O-glutaroyl derivative of VB$_{12}$ into a suitable acylating agent, such as a mixed acid anhydride, acid halide or activated ester, isolating this new derivative, and then reacting it with the protein. The preferred approach comprises the preparation and isolation of the N-hydroxysuccinimidyl active ester of the 5'-O-glutaroyl derivative of VB$_{12}$ and reacting that derivative with the therapeutic protein of interest.

b) Conducting the conjugation the 5'-O-glutaroyl derivative of VB$_{12}$ with the protein moiety in the presence of a suitable carboxyl group activating reagent, such as dihexylcarbodiimide, 1-ethyl-3-(3-dimethylaminopropyl)-carbodiimide, 1-cyclohexyl-3-(2-morpholinyl-(4)-ethyl-carbodiimide, N-benzyl-N'-3-dimetylaminopropylcarbodiimide, N-ethyl-3-phenylisoxazolium-3'-sulfonate (Woodwards Reagent K), N-ethylbenzioxazolium tetrafluoroborate, ethylchloroformate, p-nitrophenylchloroformate, 1,1'-carbonyldiimidazole, N-(ethoxycarbonyl)-2-ethoxy-1,2-dihydroquinoline, and N-(isobutylcarbonyl)-2-isobutoxy-1,2-dihydroquinoline.

c) Optionally, performing further modifications of the 5'-O-glutaroyl derivative of VB$_{12}$ at the carboxylic acid site with the goal of introducing additional functional groups which, in turn, are suitable for conjugation with proteins. This latest step could be performed in the presence of a suitable homo- or heterobifunctional reagent, if necessary. The addition of such new functionalities can serve a number of purposes. In some cases, this addition is done for the purpose of incorporating spacer arms to increase the distance between the VB$_{12}$ moiety and the protein surface in the conjugates. In other cases, the functional group transformations can be used to change the reactivity or selectivity of the VB$_{12}$-based reagent, thus changing the type or number of the protein side chain functional groups that will be involved in subsequent conjugation reactions. The importance of these manipulations is clearly demonstrated by the working examples which appear further on in this text.

In general, VB$_{12}$-protein conjugates in accordance with this invention will be useful in any of the therapies for which the protein component of the conjugates is useful. For instance, conjugates of VB$_{12}$ and EPO can be used to treat patients suffering from chronic anemia, as in cases of renal failure. Conjugates of VB$_{12}$ and G-CSF can be employed to treat neutropenia or to increase neutrophil levels to combat infection. Conjugates of VB$_{12}$ and consensus interferon can be used to combat viral infections, such as hepatitis B and hepatitis C.

The amount of the conjugate that will be effective in the treatment of a particular disorder or condition will depend on the nature of the disorder or condition, and can be determined by standard clinical techniques or dosage amounts and regimens already established for that particular protein. Where possible, it is desirable to determine the dose-response curve and the pharmaceutical compositions of the invention first in vitro, as in bioassay systems, and then in useful animal model systems prior to testing in humans.

Methods of administration include intradermal, intramuscular, intraperitoneal, intravenous, subcutaneous, intranasal, and especially, oral. Oral administration is preferred because the $VB_{12}$-protein conjugates of this invention are specifically adapted for oral delivery and enteral uptake.

The invention also provides pharmaceutical compositions comprising an effective amount of a $VB_{12}$-protein conjugate of the invention together with one or more pharmaceutically acceptable diluents, preservatives, solublizers, emulsifiers, adjuvants and/or carriers. Standard procedures for formulating the ingredients into a suitable dosage form can be used.

Pharmaceutical compositions which have been formulated or adapted for oral delivery are particularly preferred. Formulations are available that do not dissolve in the stomach, yet release the $VB_{12}$-protein in the duodenum or elsewhere in the intestinal tract. Solid dosage forms of this type include tablets, capsules, pills, troches or lozenges, cachets and pellets. Other such solid forms can encompass proteinoid (see, e.g., U.S. Pat. No. 4,925,673) or liposomal encapsulation. See, for additional details, Marshall, K., *Modern Pharmaceutics*, edited by G. S. Banker and C. T. Rhodes, Chapter 10 (1979). The solid dosage form can include the use of an enteric coating, examples of which are methacrylic acid copolymers, such as Eudragit, manufactured by Rohm Tech, Inc., Malden, Mass.; Shellac, manufactured by Montrose-Haeuser, Millmaster Onyx Group, New York, N.Y.; hydroxypropyl methylcellulose phthalate, manufactured by Biddle Sawyer Corp., New York, N.Y.; and cellulose acetate phthalate (CAP), manufactured by Eastman Chemical Products, Inc., Kingsport, Tenn. These coating materials may be used as films individually or in combination. To ensure optimum gastric resistance, coatings having stability at a pH of less than 5.0 are preferred.

Coatings or coating mixtures, including sucrose, can be used in tablets that are not intended for protection against gastric juices. Capsules of this type can consist of a hard gelatin shell for delivery of a dry therapeutic, for example, a powder, or a soft gelatin shell for delivery of a liquid therapeutic, for example, a $VB_{12}$-protein solution. The coating material for cachets can consist of starch paper. For other forms such as pills, lozenges, molded tablets or tablet triturates, moist massing techniques can be employed.

The $VB_{12}$-protein conjugates of this invention can be formulated as fine particulates in the form of granules or pellets having a very small particle size, for example, about one micron. Formulation for administration as a capsule can be in the form of a powder, lightly compressed plug, or tablet.

It may be desirable or necessary to dilute or increase the volume of the $VB_{12}$-protein conjugate with the use of a pharmaceutically inert material. Suitable diluents include carbohydrates, such as, mannitol, α-lactose, anhydrous lactose, cellulose, sucrose, modified dextrins and starch. Inorganic salts which are useful as fillers include calcium carbonate, dicalcium phosphate dihydrate, calcium triphosphate, magnesium carbonate and sodium chloride. Examples of commercially available diluents and fillers include FAST-FLO, manufactured by Foremost Foods Company, San Francisco, Calif.; STA-RX 1500, manufactured by Staley Manufacturing Company, Decatur, Ill.; EMCOMPRESS, manufactured by Edward Mandell Company, Carmel, N.Y.; AVICEL, manufactured by FMC Corporation, Philadelphia, Pa.; and LACTOSE DT, manufactured by Sheffield Products, Norwich, N.Y.

Disintegrants can be included for use in solid dosage forms according to the invention. Examples include starch, sodium starch glycolate, amberlite, sodium carboxymethylcellulose, ultramylopectin, sodium alginate, gelatin, acid carboxymethyl cellulose, natural sponge and bentonite. Other suitable disintegrant materials include insoluble cationic exchange resins, powdered gums, for example, agar, and alginic acid or alginic acid salt.

Other ingredients that can be used in the pharmaceutical composition include colorants, flavorants and binders, for example, acacia, tragacanth, starch, gelatin, methyl cellulose, polyvinyl pyrrolidone, and the like; antifrictional agents, for example, stearic acid, polytetrafluoroethylene, liquid paraffin, vegetable oils, waxes, sodium lauryl sulfate, and the like; glidants, for example, talc, pyrogenic silica, hydrated silicoaluminate, and the like; and surfactants, including, anionic detergents, such as sodium lauryl sulfate, dioctyl sodium sulfosuccinate, dioctyl sodium sulfonate, and the like, cationic detergents, such as, benzalkonium and benzethonium chloride, or nonionic detergents, such as polyoxyl stearate, polyoxyethylene hydrogenated castor oil, glycerol monostearate, polysorbate, sucrose fatty acid ester, methyl cellulose, carboxymethyl cellulose, and the like.

The aforementioned diluents, fillers, disintegrants, colorants, flavoring agents, binders, etc., can be used in amounts which are conventional for their intended purposes.

It may be desirable for some applications to utilize a controlled release dosage form from which the $VB_{12}$-protein conjugate is gradually released over an extended period of time. For instance, the $VB_{12}$-protein conjugate can be incorporated in an inert matrix, such as a gum, that permits release by diffusion or leaching. The use of a slowly degenerative matrix or semipermeable membrane is also possible. Enteric coatings, by their nature, also function to delay release.

As noted previously, the therapeutic protein can be modified by the covalent attachment of polymers, such as polyethylene glycol. Such polymers can serve to enhance protein stability for oral dosage forms. For further information, see Delgado et al., *Critical Reviews in Therapeutic Drug Carrier Systems*, Volume 9, pages 249–304 (1992). Alternatively, carrier polymers which incorporate $VB_{12}$ and the therapeutic protein by attachment to side chains of the polymer can be used as a means of delivering increased amounts of the conjugate and, concomitantly, the therapeutic.

As mentioned, absorption and uptake of the $VB_{12}$-protein conjugates in the gut after oral delivery can be significantly enhanced if the conjugate is utilized with an effective amount of natural or recombinant exogenous intrinsic factor. Accordingly, in a preferred method of practice the pharmaceutical composition is formulated to include intrinsic factor admixed as an additional ingredient. Typically, effective amounts of IF included in such compositions will be based on the amount of $VB_{12}$ conjugate employed, and in general will involve the use of a molar ratio of IF to $VB_{12}$ not exceeding 2:1.

Generally, an effective amount of the $VB_{12}$-protein conjugate of this invention will be determined by the age, weight and condition or severity of disease of the recipient. See, *Remington's Pharmaceutical Sciences*, at pages 697–773, incorporated herein by reference. Dosing may be one or more times daily, or less frequently, and may be in conjunction with other compositions, as the skilled practitioner will recognize. Because enteral uptake is enhanced by use of the conjugate, and further by use of intrinsic factor in ad mixture with the conjugate, it is expected that lower doses will be enabled to achieve the same bioavailability as the protein administered alone.

DESCRIPTION OF SPECIFIC EMBODIMENTS

The invention is further illustrated with reference to the Examples materials, methods, procedures and test results given below.

Materials

Human erythropoetin (EPO), human granulocyte colony stimulating factor (G-CSF) and human consensus interferon (IFN-Con) were produced recombinantly by Amgen Inc., Thousand Oaks, Calif., by expression of the human DNA in Chinese hamster ovary or bacterial (*E. coli*) cells. Porcine IF was obtained from Sigma Chemical Company, St. Louis, Mo. Vitamin $B_{12}$ was also obtained from Sigma. Buffers and other reagents and materials were standard.

High Performance Liquid Chromatographic Analysis

Method 1
Column: 3.9×150 millimeters (mm), Nova-Pak (C18), Waters, Millford, Mass. Mobile phase A: 50 mM phosphate, pH 6.5; mobile phase B: acetonitrile. Gradient: at t=0 minutes, 95% A and 5% B; between t=0 minutes and t=5 minutes, changed linearly to 85% A and 15% B and held until t=13 minutes; between t=13 minutes and t=27 minutes, changed linearly to 15% A and 85% B, then linear return to starting conditions between t=27 minutes and t=28 minutes. Flow rate: 1.5 milliliters per minute (ml/min). UV Detector: 360 nanometers (nm).

Method 2
Column: 4.6×250 millimeters (mm), 214 TP(C4), Vydac, Hesperia, Calif. Mobile phase A: 0.1% trifluoroacetic acid (TFA); mobile phase B: 95% acetonitrile in 0.1% TFA. Gradient: at t=0 minutes, 95% A and 5% B; between t=0 minutes and t=10 minutes, changed linearly to 70% A and 30% B; between t=10 minutes and t=55 minutes, changed linearly to 25% A and 75% B, held until t=60 minutes, then linear return to starting conditions between t=60 minutes and t=61 minutes. Flow rate: 0.8 ml/min. UV Detector: 220 nm and 360 nm.

Method 3
Column: 7.5×300 mm, UltraSpherogel SEC 2000, Beckman Co., Fullerton, Calif., two columns coupled in series. Mobile phase: 100 mM phosphate, pH 6.9. Flow rate: 1 ml/min. UV Detector: Channel 1:280 nm; Channel 2:360 nm.

EXAMPLE 1

Preparation of 5'-O-[glutaboyl]cyanocobalamin

Five grams (g) of cyanocobalamin ($VB_{12}$) were dissolved in 1,000 ml of dry dimethylsulfoxide containing 200 g of glutaric anhydride and 160 ml of pyridine. After twelve hours at room temperature (25° C.), the excess glutaric anhydride was destroyed by adding 1 liter of water while maintaining the mixture at pH 6.0 with 10% aqueous potassium hydroxide. Potassium cyanide was then added to obtain a final concentration of 10 mM, and the solution was adjusted to pH 6.0 with the addition of 3N hydrochloric acid. After one hour, the solution was added to a column (5×30 cm) packed with XAD-16 (Sigma Chemical Co.). The column was first washed with deionized water. Then cyanocobalamin derivatives were eluted with 50% aqueous acetonitrile. The eluant was evaporated in a rotary evaporator to a volume of 80 ml and applied to a AG 1×2 (Bio-Rad) column (acetate form, 200–400 mesh, 4.4×100 cm). The column was washed with water to remove unreacted cyanocobalamin. Monoglutaryl derivatives were eluted with 0.16% acetic acid. After the elution of a minor component, the eluant containing the main component was collected, desalted with XAD-16, concentrated to about 200 ml, and lyophilized. The yield was 3.5 g (65%) of 5'-O-[glutaroyl]-cyanocobalamin. HPLC analysis (Method 1) of a sample of the product showed that it was a single component.

Infrared spectrum ($KB_r$) 1714 $cm^{-1}$. Mass spectrum: M+1, 1469.74±0.35; calculated: 1469.61 m/e. Elemental analysis: calculated for $C_{68}H_{94}CON_{14}O_{17P}.9H_2O$:C, 50.06;H, 6.93;N, 12.02%. Found C,49.93; H,7.11;N, 11.94%.

EXAMPLE 2

Conjugation of 5'-O-[Glutaroyl]Cyanocobalamin to G-CSF

This Example illustrates the formation of a conjugate of 5'-O-[glutaroyl]cyanocobalamin with G-CSF by the preparation of 5'-O-[glutaroyl]cyanocobalamin N-hydroxysuccinimide and the reaction of that derivative with G-CSF.

Sixty milligrams of 5'-O-[glutaroyl]cyanocobalamin, prepared as described in Example 1, were added to a solution of 191 mg of 1-(3-dimethylaminopropyl)-3-ethylcarbodiimide hydrochloride (EDC) and 115 mg of N-hydroxysuccinimide (NHS) in 4 ml of anhydrous ethanol. The reaction mixture was stirred at room temperature for two hours, then added dropwise to 200 ml of anhydrous dichloromethane to produce 5'-O-[glutaroyl]-cyanocobalamin N-hydroxysuccinimide. The latter was collected by filtration as an amorphous, finely divided precipitate. HPLC analysis (Method 1) showed that the product was pure.

An ethanol solution of 5'-O-[glutaroyl]-cyanocobalamin-N-hydroxysuccinimide (8.5 mg/ml) was prepared, and 0.1 ml of this solution was added to a solution of 5 mg of G-CSF in 1 ml of 100 mM bicine buffer, pH 8.0. The reaction was allowed to proceed for one hour at room temperature, after which the reaction mixture was adjusted to pH 4.0 with 0.1N HCl and diluted to a protein concentration of 1 mg/ml. The resulting reaction product was separated from unreacted cyanocobalamin by elution through Sephadex G-50, Pharmacia, Piscataway, N.J., in 20 mM sodium acetate, pH 4.0. Analysis by HPLC (Method 2) revealed that the conjugate of 5'-O[glutaroyl]cyanocobalamin and G-CSF was eluted as two partially resolved components, reflecting different degrees of conjugation of G-CSF. The molar ratio of cyanocobalamin to G-CSF in these conjugates was 1.84 and 0.52, respectively.

EXAMPLE 3

Conjugation of 5'-O-[Glutaroyl]Cyanocobalamin to EPO

This Example illustrates the formation of a conjugate of 5'-O-[glutaroyl]cyanocobalamin and EPO by the reaction of 5'-O-[glutaroyl]cyanocobalamin N-hydroxysuccinimide with EPO.

0.18 ml of an ethanol solution of 5'-O-[glutaroyl]cyanocobalamin N-hydroxysuccinimide prepared as in Example 2 was added to 3 mg of EPO in 0.5 ml of 100 mM bicine buffer, pH 8.0. After two hours at 4° C. 2.5 ml of 20 mM sodium citrate buffer, pH 7.0, were added to the reaction mixture. Unreacted cyanocobalamin was separated from the resulting reaction product by elution through Sephadex G-50 in 20 mM sodium acetate, at a pH of 7.0. Analysis by HPLC (Method 3) showed that the conjugate of 5'-O-[glutaroyl] cyanocobalamin and EPO eluted as a single peak and contained a molar ratio of cyanocobalamin to EPO of 2.5.

EXAMPLE 4

Conjugation of 5'-O-[Glutaroyl]Cyanocobalamin to IFN-CON

This Example illustrates the formation of a conjugate of 5'-O-[glutaroyl]cyanocobalamin and IFN-Con by the reaction of 5'-O-[glutaroyl]cyanocobalamin N-hydroxysuccinimide with IFN-Con.

Two milligrams of IFN-Con dissolved in 2 ml of PBS, pH 7.0, was added to 5'-O-[glutaroyl]cyanocobalamin N-hydroxysuccinimide solution (0.2 ml) prepared as in Example 2. After stirring for three and one half hours at room temperature, unreacted cyanocobalamin was separated by gel chromatography on Sephacryl S-100 in the presence of the same buffer. HPLC (Method 2) showed that the resulting conjugate of IFN-Con and 5'-O-[glutaroyl]cyanocobalamin was eluted as a single peak, with a molar ratio of cyanocobalamin to IFN-Con of 3.7.

EXAMPLE 5

Preparation of 5'-O-[Glutaroyl]Cyanocobalamin-12-Aminododecylamide

This Example illustrates the preparation of the 12-aminododecylamide derivative of 5'-O-[glutaroyl]cyanocobalamin for use as an intermediate.

Sixty three milligrams of 5'-O-[glutaroyl]cyanocobalamin N-hydroxysuccinimide, prepared as in Example 2, were dissolved in 10 ml of anhydrous methanol containing 160 mg of 1,12-diaminododecane. The reaction mixture was stirred at room temperature for fifteen minutes before reducing the volume to 5 ml by vacuum evaporation. The crude product was precipitated in 500 ml of dichloromethane, filtered, than partially purified by elution through a Silica $C_4$ (Vydac) 3.2×10 cm column with a 0–100% gradient of aqueous acetonitrile containing 0.1% TFA. Further purification was achieved by elution from an S Sepharose FF 2.6×30 cm column, using a 0–100% gradient of 0.1N HCl. The resulting product, 5'-O-[glutaroyl]cyanocobalamin-12-aminododecylamide, was desalted with a Sep-Pak $C_{18}$ Cartridge (Waters) in a conventional manner, then lyophilized. The yield was 15 mg (23%). HPLC analysis of the product was by Method 1.

EXAMPLE 6

Preparation of 5'-O-[Glutaroyl]Cyanocobalamin-12-Aminododecylamido-Dithiopyridylpropionate This Example illustrates the preparation of dithiopyridylpropionate derivative of 5'-O-[glutaroyl]cyanocobalamin-12-aminododecylamide for use in the preparation of $VB_{12}$-protein conjugates.

Thirteen milligrams of N-succinimidyl 3-(2-pyridyldithio)propionate were added to 3 ml of anhydrous methanol containing 13.8 mg of 5'-O-[glutaroyl]cyanocobalamin-12-aminododecylamide prepared as described in Example 5, and 0.0016 ml of triethylamine. The reaction mixture was stirred at room temperature for thirty minutes, reduced in volume to 1 ml, then added dropwise to 300 ml of dichloromethane. The resulting precipitated product, 5'-O-[glutaroyl]cyanocobalamin-12-aminododecylamidedithiopyridylpropionate, was filtered, dissolved in 30% aqueous acetonitrite, and lyophilized. The yield was 12 mg (82%). HPLC analysis of the product was by Method 1. Mass spectrum: M+1848.50±0.70; calculated; 1847.81

EXAMPLE 7

Reaction of 5'-O-[Glutaroyl]Cyanocobalamin-12-Aminododecylamido-Dithiopyridylpropionate with G-CSF This Example illustrates the formation of a conjugate of 5'-O-[glutaroyl]cyanocobalamin with G-CSF by the reaction of 5'-O-[glutaroyl]cyanocobalamin-12-aminododecylamido-dithiopyridylpropionate with G-CSF.

4.06 mg of 5'-O-[glutaroyl]cyanocobalamin-12-aminododecylamido-dithiopyridylpropionate, prepared as in Example 6, was added to a mixture of 4 mg of G-CSF in 0.67 ml of water which had been acidified to a pH of 3.25 with hydrochloric acid. After being left standing for thirty six hours at 4° C. unreacted 5'-O-[glutaroyl]cyanocobalamin-12-aminododecylamidodithiopyridylpropionate was separated from the reaction mixture by elution through Sephadex G-50 with 20 mM sodium acetate at pH 4.0. Analysis by HPLC (Method 2) showed that the resulting conjugate of 5'-O[glutaroyl]cyanocobalamin and G-CSF eluted as a single peak, with a molar ratio of cyanocobalamin to G-CSF of 1:1.

EXAMPLE 8

Reaction of 5'-O-[Glutaroyl]Cyanocobalamin-12-Aminododecylamido-Dithiopyridylpropionate with Polyethyleneglycol Derivative of G-CSF This Example illustrates the formation of a conjugate of 5'-O-[glutaroyl]cyanocobalamin with a polyethylene glycol derivative of G-CSF by the reaction of 5'-O-[glutaroyl]-cyanocobalamin-12-aminododecylamidodithiopyridylpropionate with the derivative.

A solution was prepared of 4.06 mg of 5'-O-[glutaroyl] cyanocobalamin-12-aminododecylamidodithiopyridylpropionate (Example 6) in 0.34 ml of 50% aqueous acetonitrite. Separately, a solution was prepared of a polyethylene glycol derivative of G-CSF, containing 4.14 mg of G-CSF, in 0.81 ml of water which had been acidified to a pH of 3.25 with hydrochloric acid. The two solutions were mixed and left standing for thirty six hours at 4° C. Unreacted cyanobolamin was separated by gel chromatography using Sephadex G-50 in 20 mM sodium acetate, pH 4.0. Fractions containing G-CSF were pooled. HPLC (Method 2) showed that the resulting conjugate of 5'-O-[glutaroyl]cyanocobalamin and polyethyleneglycol-G-CSF was eluted as a single broad peak, with a molar ratio of cyanocobalamin to G-CSF of 0.89.

EXAMPLE 9

Preparation of 5'-O-[Glutaroyl]Cyanocobalamin-8-Aminocaprylic Acid

This Example illustrates the preparation of the 8-aminocaprylic acid derivative of 5'-O-[glutaroyl]cyanocobalamin for use as an intermediate in the formation of $VB_{12}$-protein conjugates.

Sixty three milligrams of 5'-O-[glutaroyl]cyanocobalamin N-hydroxysuccinimide, prepared as in Example 2, was added to 10 ml of anhydrous methanol containing 80 mg of 8-aminocaprylic acid. The reaction mixture was stirred at room temperature for thirty minutes, the volume was reduced to 5 ml by vacuum evaporation, and the crude reaction product was precipitated by the addition of 500 ml of dichloromethane. The precipitate was filtered and purified by elution from a Silica C4 (Vydac) 3.2×10 cm column, using a 0–100% gradient of acetonitrile in 1.0% TFA. Fractions containing the product were pooled, concentrated (to about 50 ml) by vacuum evaporation, lyophilized, and purified on a AG 1×2 column (acetate form, 200–400 mesh, 3.2×16 cm) with a gradient of 0–100% 0.1N acetic acid. Product fractions were concentrated with Sep-Pak C18 Cartridges (Waters), then lyophilized to give pure 5'-O-[glutaroyl]cyanocobalamin-8-aminocaprylic acid as a red powder. HPLC analysis of the product was by Method 1. Mass spectrum: M+1609.62±0.35; calculated: 1610.71 m/e.

EXAMPLE 10

Reaction of 5'-O-[Glutaroyl]Cyanocobalamin-8-Aminocaprylic Acid-N-Hydroxysuccinimide with G-CSF This Example illustrates the formation of a conjugate of 5'-O-[glutaroyl]cyanocobalamin with G-CSF by the preparation of the N-hydroxysuccinimidyl ester of 5'-O-[glutaroyl]cyanocobalamin-8-aminocaprylic acid and the reaction of that derivative with G-CSF.

Forty milligrams of 5'-O-[glutaroyl]-cyanocobalamin-8-aminocaprylic acid, prepared as in Example 9, were added to a mixture of 118 mg of 1-(3-dimethylaminopropyl)-3-ethylcarbodiimide hydrochloride and 71 mg of N-hydroxysuccinimide in 1.4 ml of anhydrous ethanol. The resulting mixture was stirred at room temperature for two hours, then added dropwise to 200 ml of anhydrous dichloromethane. The resulting product, 5'-O-[glutaroyl]cyanocobalamin-8-aminocaprylic acid-N-hydroxysuccinimide, was precipitated as an amorphous finely divided powder and collected on a 0.45 μm pore size filter.

A solution of 2.11 mg of 5'-O-[glutaroyl]cyanocobalamin-8-aminocaprylic acid-N-hydroxysuccinimide in 0.08 ml of ethanol was mixed with 4 mg of G-CSF in 0.8 ml of 100 mM bicine buffer, pH 8.0. After one hour at room temperature, the mixture was adjusted to pH 4.0 with 0.1N HCl and diluted to a protein concentration of 1 mg/ml. Unreacted cyanocobalamin was separated by gel chromatography on Sephadex G-50 by elution with 20 mM sodium acetate at a pH of 4.0. Analysis by HPLC (Method 2) revealed that the conjugate of 5'-O-[glutaroyl]cyanocobalamin and G-CSF eluted as two partially resolved peaks. The molar ratio of cyanocobalamin to G-CSF in each product was 2.72 and 1.81, respectively.

EXAMPLE 11

Reaction of 5'-O-[Glutaroyl]Cyanocobalamin-8-Aminocaprylic Acid-N-Hydroxysuccinimide with EPO This Example illustrates the conjugation of 5'-O-[glutaroyl]cyanocobalamin with EPO by the reaction of 5'-O-[glutaroyl]cyanocobalamin-8-aminocaprylic acid-N-hydroxysuccinimidyl to EPO.

A solution of 3 mg of EPO in 0.5 ml of 100 mM bicine buffer, pH 8.0, was added to 1.70 mg of 5'-O-[glutaroyl] cyanocobalamin-8-aminocaprylic acid-N-hydroxysuccinimide prepared as in Example 10. After the mixture was left standing for two hours at 4° C., 2.5 ml of 20 mM sodium citrate buffer, pH 7.0, were added and unreacted cyanocobalamin was separated by gel chromatography on Sephadex G-50 in the presence of the same buffer. Analysis by HPLC (Method 3) showed that the conjugate of 5'-O-[glutaroyl] cyanocobalamin-8-aminocaprylic acid and EPO eluted as a single peak and had a molar ratio of cyanocobalamin to EPO of 3.00.

EXAMPLE 12

Preparation of 5'-O-[Glutaroyl]Cyanocobalamin-Adipic-1,6-Dihydrazide

This Example illustrates the preparation of the adipic-1,6-dihydrazide derivative of 5'-O-[glutaroyl]cyanocobalamin for use as an intermediate in the preparation of $VB_{12}$-protein conjugates.

Sixty three milligrams of 5'-O-[glutaroyl]cyanocobalamin N-hydroxsuccinimide, prepared as in Example 2, were added to a solution of 139 mg of adipic-1,6-dihydrazide in 10 ml of anhydrous methanol. The solution was stirred at room temperature for three hours, the volume was reduced to 5 ml by vacuum evaporation, and the crude product was precipitated by the addition of 500 ml of dichloromethane. The precipitated product was dissolved in 5 ml of 0.1% TFA, then eluted through a Silica $C_4$ (Vydac) 3.2×10 cm column using a 0–100% gradient of acetonitrile and 0.1% TFA. Fractions corresponding to the major component were pooled, concentrated (to 50 ml) by vacuum evaporation, lyophilized, and then applied to an S Sepharose FF 2.6×30 cm column. Elution with a 0–100% gradient of 0.1 N HCl resulted in 5'-O-[glutaroyl]cyanocobalamin-adipic-1,6-dihydrazide, which was desalted using a Sep-Pak $C_{18}$ Cartridge (Waters) and lyophilized. The yield was 32 mg (50%).

EXAMPLE 13

Reaction of 5'-O-[Glutaroyl]Cyanocobalamin-Adipic-1,6-Dihydrazide with EPO

This Example illustrates the formation of a conjugate of 5'-O-[glutaroyl]cyanocobalamin with EPO by the reaction of 5'-O-[glutaroyl]cyanocobalamin-adipic-1,6-dihydrazide with EPO.

Six milligrams of EPO in 1 ml of 20 mM citrate buffer, pH 7.0, was treated with 0.3 ml of 0.1M sodium iodate at 4° C. for ten minutes. The product was buffer exchanged by elution through a Sephadex G-25 column with 0.2M sodium acetate, pH 5.5. The elution product was combined with a solution of 2.7 mg of 5'-O-[glutaroyl]cyanocobalamin-adipic acid-1,6-dihydrazide in 5.3 ml of 0.2M sodium acetate, then stirred for ten hours at 4° C. Unreacted cyanocobalamin was separated by gel chromatography on Sephacryl S-200 HR in 20 mM sodium citrate and 100 mM NaCl, pH 7.0. Analysis by HPLC (Method 3) showed that the conjugate of 5'-O-[glutaroyl]cyanocobalamin and EPO eluted as a single peak. The molar ratio of cyanocobalamin to EPO was 1.76.

EXAMPLE 14

Conjugation of 5'-O-[Glutaroyl]Cyanocobalamin-Adipic-1,6-Dihydrazide to IFN-CON This example illustrates the formation of a conjugate of 5'-O-[glutaroyl]cyanocobalamin with IFN-Con through the use of carboxylic acid functional groups on the protein.

A solution of 2 mg of IFN-Con in 2 ml of 100 mM phosphate buffer, pH 6.0, was reacted with 1.6 mg of 5'-O-[glutaroyl]cyanocobalamin-adipic-1,6-dihydrazide (prepared as in Example 12) and 1.91 mg of 1-(3-dimethyl aminopropyl)-3-ethylcarbodiimide hydrochloride for ten hours at 4° C. Then, 3.82 mg of 1-(3-dimethylaminopropyl)-3-ethylcarbodiimide hydrochloride were added and the reaction was continued under the same conditions for five more hours. Unreacted cyanocobalamin was separated from the conjugate reaction product by gel chromatography on Sephadex G-50 in the same buffer. Analysis by HPLC (Method 2) showed that the resulting conjugate of 5'-O-[glutaroyl]cyanocobalamin and IFN-Con was eluted as two partially resolved peaks, with a molar ratio of cyanocobalamin to IFN-Con of 1.8.

EXAMPLE 15

Reaction of 5'-O-[Glutaroyl]Cyanocobalamin-Adipic-1,6-Dihydrazide with EPO

This Example illustrates a second method for the formation of a conjugate of 5'-O-[glutaroyl]-cyanocobalamin with EPO through the use of the hydrazidyl functional group of a $VB_{12}$ derivative.

A solution of 2 mg of EPO in 0.36 ml of water was reacted with 1.07 mg of 5'-O-[glutaroyl]cyanocobalamin-adipic-1,6-dihydrazide (prepared as in Example 12) and 1 milligram of 1-(3-dimethylaminopropyl)-3-ethylcarbodiimide hydrochloride for fifteen hours at 4° C. Unreacted cyanocobalamin was separated from the reaction product by gel chromatography on Sephacryl S-100 in a buffer of 20 mM sodium citrate and 100 mM sodium chloride, pH 7.0. HPLC analysis (Method 3) of the reaction product, a conjugate of 5'-O-[glutaroyl]cyanocobalamin-adipic-1,6-dihydrazide and EPO, showed that the conjugate eluted as a single peak and had a molar ratio of cyanocobalamin to EPO of 0.44.

ANALYTICAL PROCEDURES AND TESTING METHODS

Intrinsic Factor Binding Affinity

The binding affinity of conjugates of $VB_{12}$ and therapeutic proteins to intrinsic factor (IF) was determined using a competition binding assay based on the procedure described by Mathan et al. in the *Journal of Clinical Investigation*, Volume 54, pages 598–608 (1974). The assay was conducted in phosphate buffered saline (PBS) containing 1 mM calcium chloride, 0.5 mM magnesium chloride and 1% by weight of bovine serum albumin (BSA) devoid of IF and cyanocobalamin (Sigma Chemical Company, St. Louis, Mo.). Porcine IF (final concentration 1.845 nM) was added to a large excess of the $VB_{12}$-protein conjugate (123 nM), together with a range of concentrations of $^{57}$Co-cyanocobalamin (0.123 mM to 12.3 nM), specific activity 10–20 µCi/µg, in a final volume of 600 µl of PBS. The solution was vortexed and incubated at room temperature for thirty minutes, before adding 1 ml of freshly prepared dextran-coated charcoal (0.5% by weight of charcoal, 0.1% by weight of dextran in PBS) at 4° C. After incubation for ten minutes, the mixture was centrifuged for fifteen minutes at 1000×G (2500 rpm) and 4° C. in a IEC Centra-8R benchtop centrifuge, VWR Scientific, South Plainfield, N.J. The supernatant was decanted from the resulting pellet and assayed in a Cobra 2000 Gamma counter (Hewlett-Packard, Palo Alto, Calif.) to determine the amount of bound $^{57}$Co-cyanocobalamin.

The ratio of bound to free $^{57}$Co-cyanocobalamin versus the bound concentration of $^{57}$Co-cyanocobalamin was plotted according to the method of Scatchard, *Annals of the New York Academy of Science*, Volume 51, pages 660–672 (1949). The binding affinities of 5'-O-[glutaroyl]-cyanocobalamin and its protein conjugates to porcine IF were determined from the slope of the Scatchard plot using the following equation:

$$-\text{Slope} = -K_{app} = -K_L/(1+K_c[L_f])$$

in which $K_c$=binding affinity of conjugate $K_L$=binding affinity of cyanocobalamin $[L_f]$=concentration of unbound conjugate The use of a large excess of the conjugate permitted the value of $[L_f]$ to be treated as a constant (123 nM). The value of $K_L$ determined from the mean of six assays was $(6.02\pm0.90)\times10^9$M.

In Vitro Biological Activity of $VB_{12}$-G-CSF Conjugates

The bioactivity of $VB_{12}$-G-CSF in vitro after conjugation to 5'-O-[glutaroyl]cyanocobalamin was determined by measuring the stimulated in vitro uptake of $^3$H-thymidine into mouse bone marrow cells.

Bone marrow cells were collected from the hind legs of female Balb/C mice by flushing the bone with PBS. The cells were purified on a Ficoll-Paque density gradient (Pharmacia) and cultured in McCoys' 5A medium with 10% fetal bovine serum (FBS), 10 mM sodium pyruvate, 1×minimum essential medium (MEM) amino acids, 40 micromolar (µM) of essential amino acids, 0.04% by weight of sodium bicarbonate, 1×MEM vitamin solution, 10 mM L-glutamine and 0.005% by weight of gentamicin sulfate. After incubation for two hours at 37° C. under a 5% carbon dioxide-containing atmosphere, non-adherent cells were collected in the supernatant and the number of viable cells was counted in a hemocytometer.

A standard curve was prepared over a range from 0.07 to 1500 Units of G-CSF per milliliter (U/ml), and the complexes were diluted to about 0.3 to 30 U/ml prior to being assayed. To a 96-well plate was added, in triplicate, 100 µl of the standard or test material and 100 µl of culture medium containing 4×10$^4$ non-adherent mouse bone marrow cells. After incubating the plates for sixty eight hours at 37° C. under a 5% carbon dioxide atmosphere, 0.5 µCi of thymidine [methyl-3H], 20 Ci/mmol (NEN, Boston, Mass.) was added to each well. The plates were incubated as before for an additional five hours. The cells were collected on filter paper, rinsed with water (ten times) and ethanol (one time), and then counted in Biofluor scintillation fluid in a beta plate scintillation counter (LKB, Piscataway, N.J., Model 1205-001).

The bioactivity of the test material, in Units per milligram (U/mg), was determined from the standard curve of the G-CSF stimulated uptake of thymidine [methyl-$^3$H].

In Vivo Biological Activity of $VB_{12}$-EPO Conjugates

The hematopoietic activity of EPO after conjugation to 5'-O-[glutaroyl]cyanocobalamin was determined in vivo in exhypoxic polycythemic mice using the procedure of Cotes and Bingham described in *Nature*, Volume 191, pages 1065–1067 (1961).

The dilution of the complexes prior to intraperitoneal (i.p.) injection was based on the protein content derived from the $A_{280}$ of the sample.

In Vitro Biological Activity of $VB_{12}$-IFN-Con Conjugates

The in vitro bioactivity of IFN-Con after conjugation to 5'-O-[glutaroyl]cyanocobalamin was determined by measurement of the inhibition of viral replication in a cultured cell line.

HeLa cells were plated into 96-well plates at 15,000 cells/well and incubated for twenty four hours at 37° C. under 5% carbon dioxide in base medium (Dulbecco's modified Eagles medium (DMEM), containing 100 units/ml of penicillin, 100 mg/ml of streptomycin, 2 mM L-glutamine, 1% by weight of non-essential amino acids, 0.1% by weight of gentamicin sulfate and 1% HEPES buffer), with 10% FBS. IFN-Con was prepared at multiple dilutions ranging from 40 to 0.02 ng/ml (40,000 to 19.53 Units) in base medium and 0.2% FBS. One hundred microliters of each standard and appropriately diluted test sample were added to each well. For both the positive (no IFN-Con) and negative (no virus) controls, 100 µl of base medium alone was added. After further incubation for nineteen to twenty three hours, the medium was aspirated and replaced with 100 µl of the challenge virus, i.e., Encephalomyocarditis Virus (EMCV), at a dilution equal to 100–1000 tissue culture infected dose (TCID) units in DMEM with 1% FBS. The plates were further incubated for about twenty two hours, the medium was removed, and the cells were fixed with 200 µl of anhydrous methyl alcohol for five minutes.

The fixative was removed and the cells were stained for thirty minutes in 0.5% Gentian dye, then rinsed free of dye and air-dried for one half to two hours. The dye was eluted with 200 µl of ethylene glycol monomethyl ether and shaken for thirty minutes. The absorbance of each well at 650 nm was determined in a Vmax Kinetic Microplate Reader, model 88026 (Molecular Devices). The results for the standard were graphed as the log concentration of IFN-Con versus the percentage of dye uptake. Regression analysis of the linear portion of the curve between 10–83% dye uptake was performed, and the bioactivity of the test sample was determined.

RESULTS

The conjugates of $VB_{12}$ and proteins, prepared in accordance with the Examples, were evaluated for their binding affinity to the $VB_{12}$ transporting protein, intrinsic factor (IF), and for biological activity using the test procedures described above. The results are reported in Table 1.

TABLE 1

Binding Affinity of $VB_{12}$ - Protein Conjugates to Intrinsic Factor (IF); Biological Activit of $VB_{12}$ - Protein Conjugates

| Conjugate | Protein | Binding Affinity to IF ($\times 10^9$ M$^{-1}$) | Biological Activity of Conjugate[d] |
|---|---|---|---|
| $VB_{12}$ alone (control) | None | 6.0 ± 0.90 | Not Applicable |
| Example 1 | None | 0.74 | Not Applicable |
| Example 2 | G-CSF | 0.45 | n/d |
| Example 3 | EPO | n/d | 0.2%[b] |
| Example 4 | IFN-Con | 0.59 | 24 ± 4.2%[c] |
| Example 7 | G-CSF | 0.25 | 33%[a] |
| Example 8 | PEG-G-CSF | 0.093 | 4.4% of G-CSF[a] |

TABLE 1-continued

Binding Affinity of $VB_{12}$ - Protein Conjugates to Intrinsic Factor (IF); Biological Activit of $VB_{12}$ - Protein Conjugates

| Conjugate | Protein | Binding Affinity to IF ($\times 10^9$ M$^{-1}$) | Biological Activity of Conjugate[d] |
|---|---|---|---|
| Example 10 | G-CSF | 0.53 | 38% of PEG-G-CSF[a] 60%[a] |
| Example 11 | EPO | n/d | 1%[b] |
| Example 13 | EPO | 5.20 | 33 ± 14%[b] |
| Example 14 | IFN-Con | 0.52 | 28 ± 7.1%[c] |
| Example 15 | EPO | 3.10 | 63 ± 25%[b] |

[a] in vitro thymidine uptake assay
[b] in vivo exhypoxic polyethemic mouse assay
[c] in vitro viral inhibition assay
[d] % activity compared to non-conjugated protein
n/d not determined It is evident from the data listed in the Table that conjugation via the 5-O'-glutaryl group results in some reduction in the IF binding affinity. However, the $K_a$ values are still large. A range of binding affinities of IF for the protein-conjugated $VB_{12}$ are shown in Table 1. The lowest $K_a$ is $9.3 \times 10^7$ M., (Example 8); steric hindrance of the IF binding by the PEG molecules could account for this loss. The greatest retention of $VB_{12}$ binding affinity for IF is $5.2 \times 10^9$ M (Example 13), which is conjugation of $VB_{12}$ through the sialic acids of the EPO molecule. These values correspond to a retention of 1.6% and 87% of non-conjugated $VB_{12}$ binding affinity, respectively, and demonstrate that the protein-conjugated $VB_{12}$ will still bind to intrinsic factor.

The in vitro bioactivities of $VB_{12}$-conjugated G-CSF are shown, and reflect the ability of the conjugate to bind to the G-CSF receptor and, therefore, to elicit a response. The bioactivity of $VB_{12}$ conjugated G-CSF ranges from 33% to 60%. Previous studies have shown only a partial correlation between in vitro bioactivity and in vivo bioactivity. However, in most cases G-CSF with measurable activity in vitro is capable of stimulating a response in vivo.

Conjugation of 5-O'-[glutaroyl]cyanocobalamin to EPO through either the carboxy (Example 15) or sialic acid groups (Example 13) produced conjugates that were consistently active in the exhypoxic polycythemic mice assay. The activities ranged from 33% to 63%.

A similar result was observed for conjugates of IFN-Con, where $VB_{12}$ was conjugated via either the amine (Example 4) or the carboxy (Example 14) groups. The resulting conjugates had very similar bioactivities as measured in the viral inhibition studies, with 24–28% bioactivity as compared to native IFN-Con.

The foregoing test results show that the conjugation of $VB_{12}$ to the therapeutic proteins EPO, G-CSF and IFN-Con resulted in biologically active molecules. Also, the $VB_{12}$-protein conjugates were fully capable of binding to IF. The retention of IF binding affinity is essential to the development of any oral $VB_{12}$-mediated delivery.

In Vivo Biological Testing of $VB_{12}$-IFN-CON Conjugate

Additional tests involving administration of a conjugate of $VB_{12}$ and IFN-Con to animals are described below. The conjugate used was that of Example 14.

Radiolabelling of IFN-Con and $VB_{12}$-IFN-Con Conjugate

One iodobead (Pierce Chemicals, Rockford, Ill.) was prewashed with one milliliter (ml) of PBS [25 millimolar (mM) sodium phosphate, 100 mM sodium chloride, pH 6.7] in accordance with the manufacturer's instructions. The bead was then dried and placed in an Eppendorf tube with 100 microliters (μl) of 0.5M sodium phosphate buffer. To the bead was added 25 μl of $Na^{125}I$ (carrier free, specific activity 100 mCi/ml), obtained from E. I. DuPont DeNemours, Wilmington, Del., and the mixture was allowed to incubate for five minutes at room temperature. One hundred and fifty micrograms of either IFN-Con or $VB_{12}$-IFN-Con conjugate in PBS were added to the Eppendorf tube, mixed gently, and then incubated at room temperature for fifteen minutes. Thirty microliters of 1M parahydroxybenzoate were added to bind nonlabelling $^{125}I$, and the mixture was incubated for an additional ten minutes on ice. Separation of the $^{125}I$-labelled protein and the unbound $^{125}I$ was carried out on a PD10 column (Pharmacia, Piscataway, N.J.) which had been pre-equilibrated with PBS. Fractions eluted with PBS (500 μl) were collected and evaluated for radioactivity in a Cobra 5000 gamma counter (Hewlett-Packard, Downers Grove, Ill.).

The fractions containing the labeled protein were pooled and exhaustively dialyzed at 4° C. in PBS. The dialysate was continually monitored for $^{125}I$, until no more unbound $^{125}I$ was removed. The amount of free $^{125}I$ mixed with the radiolabelled protein was determined by precipitation with a final 6% solution of trichloracetic acid (TCA). The amount of non-labelling $^{125}I$ was less than 2% and the amount of IFN-Con was determined by U.V. absorption at $A_{280}$. The specific activity of the $^{125}I$-labelled IFN-Con was $3.08 \times 10^5$ cpm/μg and of the $^{125}I$-labelled $VB_{12}$-IFN-Con conjugate was $4.67 \times 10^5$ cpm/μg.

IFN-Con ELISA

Ninety six well plates were coated with 100 μl per well of a 1:1000 diluted rabbit-derived polyclonal antibody to IFN-Con (Amgen Inc., Thousand Oaks, Calif.) in 15 mM of sodium carbonate and 35 mM of sodium bicarbonate, pH 9.2. Coating was effected by incubation with the antibody at room temperature for two hours followed by incubation overnight at 4° C. After decantation, 300 μl of a blocking solution, composed of PBS containing 5% bovine serum albumin (BSA) and 0.1% of $NAN_3$, was incubated in the wells at room temperature for one hour. Fifty microliters of a TNE buffer, composed of 50 mM Trizma base, pH 7.4, containing 150 mM of NaCl, 13 mM of EDTA and 0.25 mM of thimerosol, with 0.1% Tween 20, was added to the wells together with 50 μl of standard or diluted sample. Standard curves were established in the assay using either native IFN-Con or $VB_{12}$-IFN-Con conjugate, depending on what was administered to the test rat. The EIA plates were then incubated for two hours at room temperature and for an additional two hours at 37° C. After decantation, the plates were washed twice with a standard washing solution (Kirkegaard & Perry Laboratories, Gaithersburg, Md., Cat. No. 50-63-00). A mouse monoclonal antibody to IFN-Con (Amgen Inc., Thousand Oaks, Calif.), diluted 1:4000 in TNE buffer with 10% FBS, was added and the sample was incubated overnight at room temperature. After decantation, the EIA plate was washed twice and a goat-derived anti-mouse IgG antibody, conjugated with horse radish peroxidase (HRPO), (Boehringer Mannheim, Indianapolis, Ind.), was added at a dilution of 1:2000. After incubation for two hours at room temperature, the plates were decanted and washed four times. One hundred microliters of TMB peroxidase substrate solution (Kirkegaard & Perry Laboratories, Cat. No. 50-76-00) were then added and the sample was incubated for five minutes at room temperature. The reaction was terminated by the addition of 100 μl of 1M $H_3PO_4$, and the absorbance was measured at 450 nm, referenced against the absorbance at 630 nm.

(1) Intraduodenal Administration of $VB_{12}$-IFN-Con Conjugate To Rats

Male Sprague-Dawley rats, weighing 250–350 grams each, were quarantined for seven days prior to use, then anesthetized intraperitoneally with 50 mg/kg of Nembutol. Stomachs were exposed through midline incision (approximately 3–4 centimeters) just below the Xiphoid process. A purse string suture was made in the duodenum one centimeter distal to the pylorus, and an incision of approximately two millimeters was made in the center of the suture. A ten centimeter silastic catheter was then advanced eight centimeters into the duodenum and secured in place by closing the purse string suture while being careful that the catheter was not also closed.

To ensure optimum uptake from the gut, slow release from an Alzet mini-osmotic pump, Model 2001D, over a twenty four hour period was used for infusion of 8–9 μl/hr of test sample. Pumps were prefilled under sterile conditions with the total dose indicated in 221 μl of PBS, attached at the free end of the catheter, and placed in the peritoneal cavity. Radiolabelled test samples were formulated as follows:
Group 1 (IFN-Con, Control)
$^{125}I$-IFN-Con at 10 μg/kg ($9.3 \times 10^5$ cpm/rat)+0.1% rat albumin
Group 2 ($VB_{12}$-IFN-Con Conjugate) $^{125}I$-$VB_{12}$-IFN-Con at 10 μg/kg ($1.4 \times 10^6$ cpm/rat)+0.1% rat albumin At the end of the surgery, the peritoneum was closed in each instance with a running silk suture and the skin incision was closed with wound clips. Rats were then placed on a warming pad until they recovered from anethesia.

Blood samples were withdrawn through the tail vein using isofluorane anesthesia. The amount of total radioactivity was determined for each blood sample using gamma counter. Plasma samples were also prepared by centrifugation in an Eppendorf centrifuge at 12,000 rpm, 11750×g, for fifteen minutes, and the number of TCA-precipitable counts (final 6% solution of TCA), were determined in the plasma to assess the amount of radioactivity associated with intact IFN-Con in the plasma.

Figure 7:
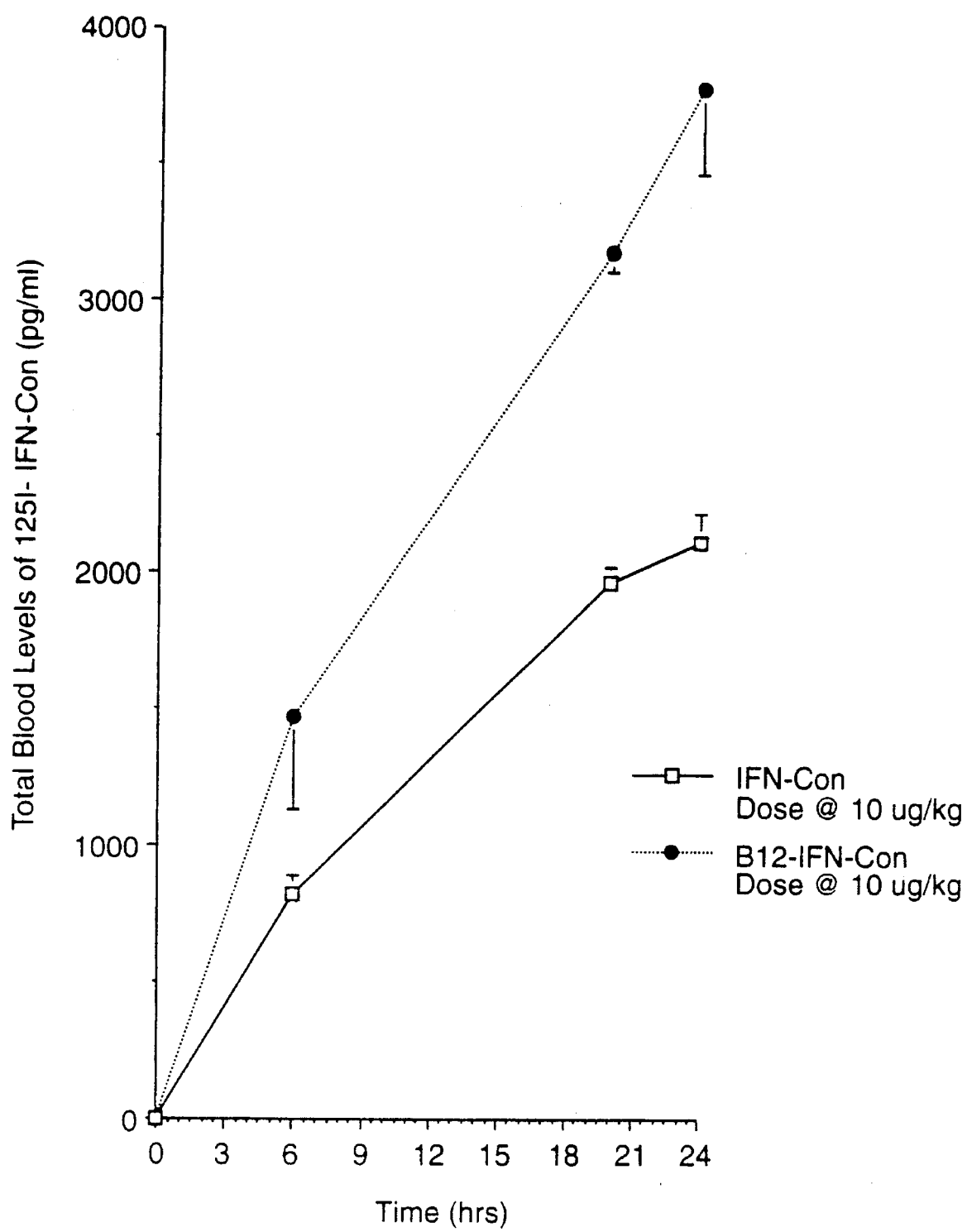
FIG. 7 is a graphical representation of the whole blood levels of IFN-Con, in picograms per milliliter, following an intraduodenal infusion of non-conjugated IFN-Con and a conjugate of $VB_{12}$ and IFN-Con.
Figure 8:
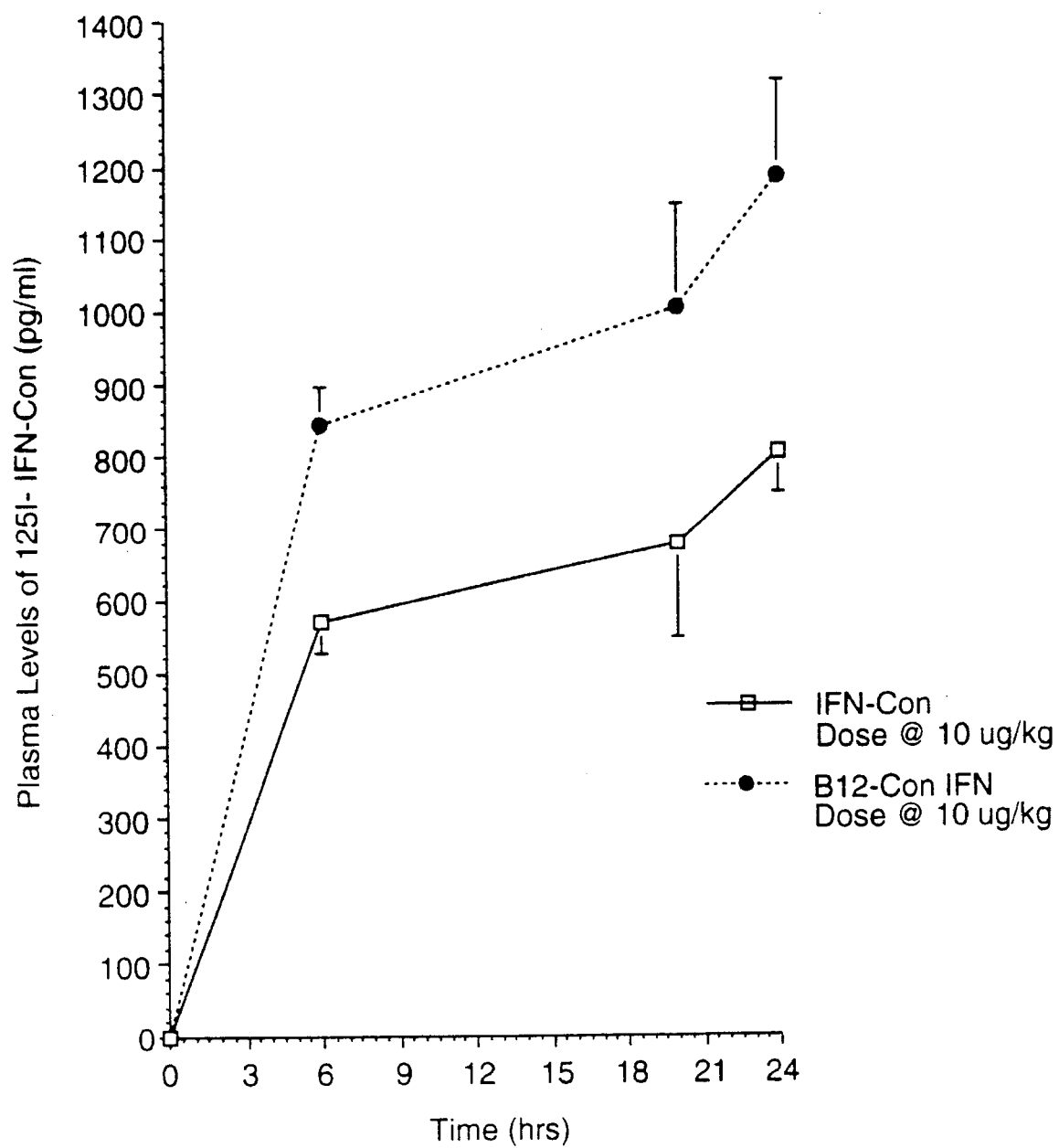
FIG. 8 is a graphical representation of the plasma levels of TCA-precipitable IFN-Con, in picograms per milliliter, following an intraduodenal infusion of non-conjugated IFN-Con and a conjugate of $VB_{12}$ and IFN-Con.

The results in FIG. 7 represent the amount of IFN-Con that was present in whole blood, i.e., plasma and blood cells, as determined from the total CPM. Some of the $^{125}I$-labelled IFN-Con might be bound to receptors present on the surface of some cells. However, it was not possible to determine if all of the counts were associated with intact protein. For this reason, a comparison of the plasma levels of TCA-precipitable protein after intraduodenal infusion is shown in FIG. 8. In looking at the data, one can see that there is an increase in plasma levels of the $VB_{12}$-conjugated protein over the non-conjugated IFN-Con. During the twenty four hour infusion period into the duodenum, the $VB_{12}$-conjugated protein reached plasma levels almost two-fold greater than for the native IFN-Con. It is somewhat surprising that the proteins did not reach a steady state during the infusion period, but instead appear to accumulate in the circulation over time. Conjugation of $VB_{12}$ with IFN-Con thus resulted in enhanced systemic delivery of the protein from the gut.

(2) Co-Administration of $^{57}CO$-$VB_{12}$ with IF

Co-administration of $^{57}Co$-$VB_{12}$ and IF to rats, using three different routes of delivery, was employed to determine if the presence of IF results in increased uptake of VB12. Some test rats were given radiolabelled $VB_{12}$ by means of the intraduodenal pump infusion method. Another group of test rats were given $^{57}Co$-$VB_{12}$ as an intraduodenal bolus. This was done using the same intraduodenal administration procedure described above. Adaptions were as follows: using a 1 cubic centimeter syringe with tubing adaptor connected to the end of the catheter, samples were injected into the duodenum in 200 μl of PBS, the catheter was withdrawn, and the suture was closed tightly. Other test rats were administered by oral gavage feeding. A recombinant form of rat IF (rrIF) produced in Chinese hamster ovary cells, was employed for those test groups designated for co-administration. A binding analysis of the rrIF prior to these in vivo studios demonstrated that the transport protein was active. The binding affinity (Ka) of rrIF was calculated to be $8.58 \times 10^9 M^{-1}$. This value is similar to that of native human IF, $2 \times 10^{10} M^{-1}$; Stupperich, E. and Nexo, E., *European Journal of Biochemistry*, Volume 199, pages 299–303 (1991). The data showed that rrIf is a good indicator of the results to be expected with porcine or human IF in a clinical setting. The animals were housed in metabolic cages and the feces collected over a forty-eight hour period to determine the amount of non-absorbed $^{57}$Co-labelled $VB_{12}$. Six test groups were evaluated, as follows:

| Group | Mode of Treatment | Routes of Administration |
|---|---|---|
| 1 | $^{57}$Co-$VB_{12}$ alone (20 ng at $6.6 \times 10^5$ dpm) | Intraduodenal pump |
| 2 | $^{57}$Co-$VB_{12}$ + IF (20 units/rat) | Intraduodenal pump |
| 3. | $^{57}$Co-$VB_{12}$ alone | Intraduodenal bolus |
| 4. | $^{57}$Co-$VB_{12}$ + IF | Intraduodenal bolus |
| 5. | $^{57}$Co-VB alone | Oral gavage |
| 6. | $^{57}$Co-$VB_{12}$ + IF | Oral gavage |

Figure 9:
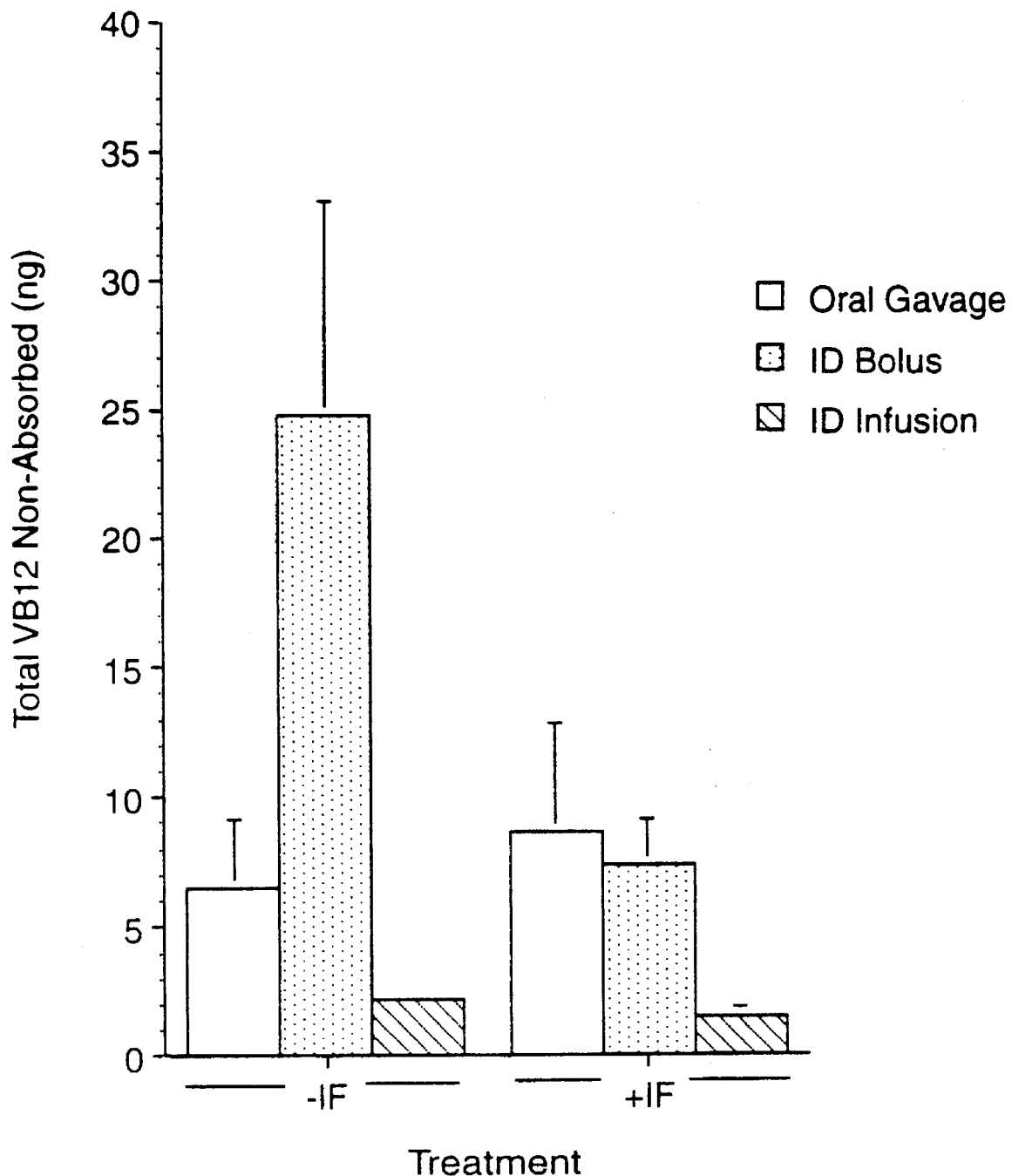
FIG. 9 shows the uptake of $^{57}$Co-labelled $VB_{12}$ in healthy rats in the presence and absence of rat intrinsic factor (rIF), following administration via oral gavage, intraduodenal bolus or intraduodenal infusion.

The results are shown in FIG. 9. As can be seen, the best method of administration of $VB_{12}$ to the gastrointestrial tract appears to be via intraduodenal infusion, with a small increase in uptake in the presence of exogenous IF. The inclusion of IF had the least effect for those animals fed by oral gavage. The greatest effect of IF occurred with administration by intraduodenal bolus. Here, uptake of $VB_{12}$ was very poor without IF, while the inclusion of IF resulted in an increase in uptake of almost three-fold, to levels similar to those achieved with oral gavage feeding. These results suggest that the inclusion of IF may enhance the uptake of a $VB_{12}$-protein conjugate. This would be especially appropriate for an oral formulation which includes an enteric coating where release of the $VB_{12}$-protein conjugate would occur in the small intestine and not in the stomach.

(3) Co-Administration of $VB_{12}$-IFN-Con with IF

Figure 10:
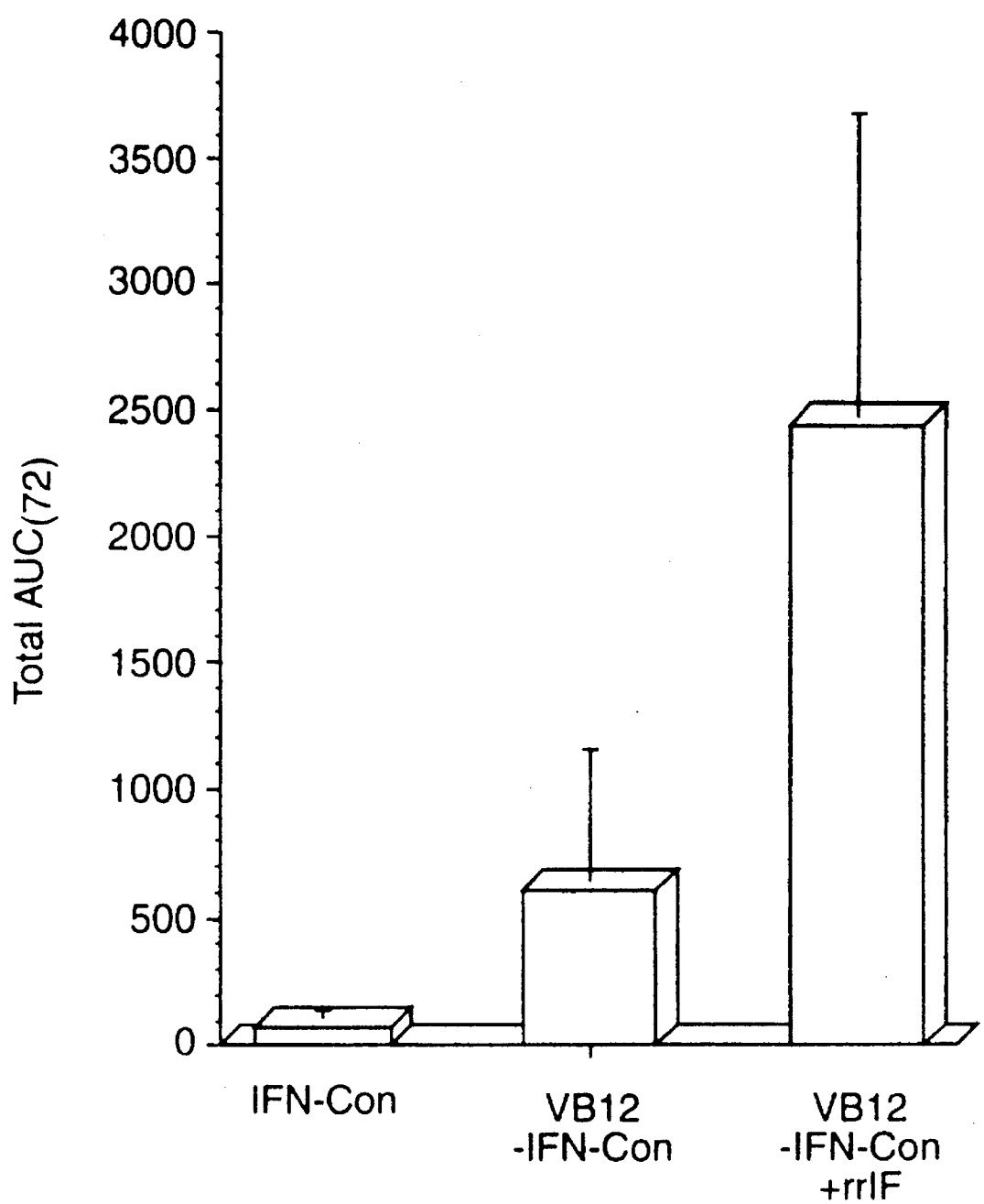
FIG. 10 shows the effect of $VB_{12}$ conjugation with IFN-Con on plasma levels of IFN-Con after intraduodenal infusion in healthy rats. The effect of the inclusion of recombinant rat intrinsic factor (rrIF) on $VB_{12}$-IFN-Con uptake is shown. The data represent the area under the plasma drug concentration level/time curve over a seventy two hour period ($AUC_{72}$), and are derived using the trapezoid rule (n=4).

Using the intraduodenal pump infusion in vivo model, native IFN-Con or $VB_{12}$-IFN-Con, was administered over twenty four hours to live, healthy rats. The dose was 500 µg/kg in PBS in each case. To evaluate the absorption enhancing effect, if any, of intrinsic factor, a third group of rats was given recombinant rat IF (3 mg/kg, or 1 mg/rat) together with $VB_{12}$-IFN-Con. The first two test groups were dosed using a single Alzet mini-osmotic pump. The third test group was dosed by placing the $VB_{12}$-IFN-Con in one Alzet mini-osmotic pump, and recombinant rat IF in another Alzet mini-osmotic pump. The two pumps were joined via a 2-centimeter catheter to a three-way tubing adaptor. The two materials were thus pre-mixed before they entered the duodenum. The ELISA was then carried out on serum taken from the test animals to determine the level of IFN-Con. Plasma samples were collected in microcontainer serum separator tubes, Becton Dickinson Co., Franklin Lakes, N.J., and stored at −80° C. prior to analysis. An AUC analysis was performed out to seventy two hours after the beginning of the study ($AUC_{72}$). The results are summarized in FIG. 10.

As can be seen, the $AUC_{72}$ for $VB_{12}$-IFN-Con conjugate was increased by ten-fold over native IFN-Con. Those animals given a combination of $VB_{12}$-IFN-Con and recombinant rat intrinsic factor experienced an even greater elevation of IFN-Con in their sera, specifically, a thirty-six fold increase over native IFN-Con and a four-fold increase over $VB_{12}$-IFN-Con without IF. These data show that, once again, a $VB_{12}$-protein conjugate has enhanced enteral uptake as compared to the non-conjugated protein. Also, the uptake capacity of a $VB_{12}$-based delivery system is greatly enhanced by the inclusion of the transporting protein, IF.

(4) Intravenous Administration of $VB_{12}$-IFN-Con Conjugate to Rats

A) Pharmacokinetics

An indwelling cannula was implanted in the right jugular vein of male Sprague Dawley rats weighing 250 grams and the test animals were allowed to recover for one day prior to administration of the test samples. The cannulas were flushed twice daily with 100 µl of saline containing 30 U/ml of heparin. Two groups of rats were used, three rats to a group, which were dosed through the penile vein with the following formulations:

Group 1 (IFN-Con, Control)

$^{125}$I-IFN-Con at 8.2 µg/rat or 33 µg/kg; specific activity 486 cpm/ng or $4.0 \times 10^6$ cpm/rat; volume of injection=120 µl/rat Group 2 ($VB_{12}$-IFN-Con Conjugate)

$^{125}$I-$VB_{12}$-IFN-Con at 0.4 µg/rat or 1.6 µg/kg; specific activity 1170 cpm/ng or $4.0 \times 10^6$ cpm/rat; volume of injection=100 µl/rat All samples were formulated in PBS. Blood samples were collected through the indwelling cannula, and the amount of radioactivity in each sample was determined in a Cobra 5000 gamma counter (Packard).

B) Biodistribution

Three time points, 5 minutes, 60 minutes and 6 hours, were selected for biodistribution analysis following intravenous administration of the following formulations into the penile vein:

Group 1 (IFN-Con, Control)

$^{125}$I-IFN-Con at 4.0 µg/rat or 16 µg/kg; specific activity 486 cpm/ng or $2.0 \times 10^6$ cpm/rat; volume of injection=100 µl/rat Group 2 ($VB_{12}$-IFN-Con Conjugate)

$^{125}$I-$VB_{12}$-IFN-Con at 4.0 µg/rat or 16 µg/kg; specific activity 500 cpm/ng or $2.0 \times 10^6$ cpm/rat; volume of injection=100 µl/rat After the animals were sacrificed, vital organs were removed and either the whole organ or a weighed portion was counted in the gamma counter, with the results then corrected for overall weight of the organ. For estimation of the total amount of IFN-Con in the blood, 1 milliter of whole blood was counted and a total volume of 17 milliliters was assumed for a rat weighing 250 grams to determine the level of IFN-Con that might be associated with the gut, a 10-centimeter section of the duodenum was removed and counted in the gamma counter.

Results

Figure 11:
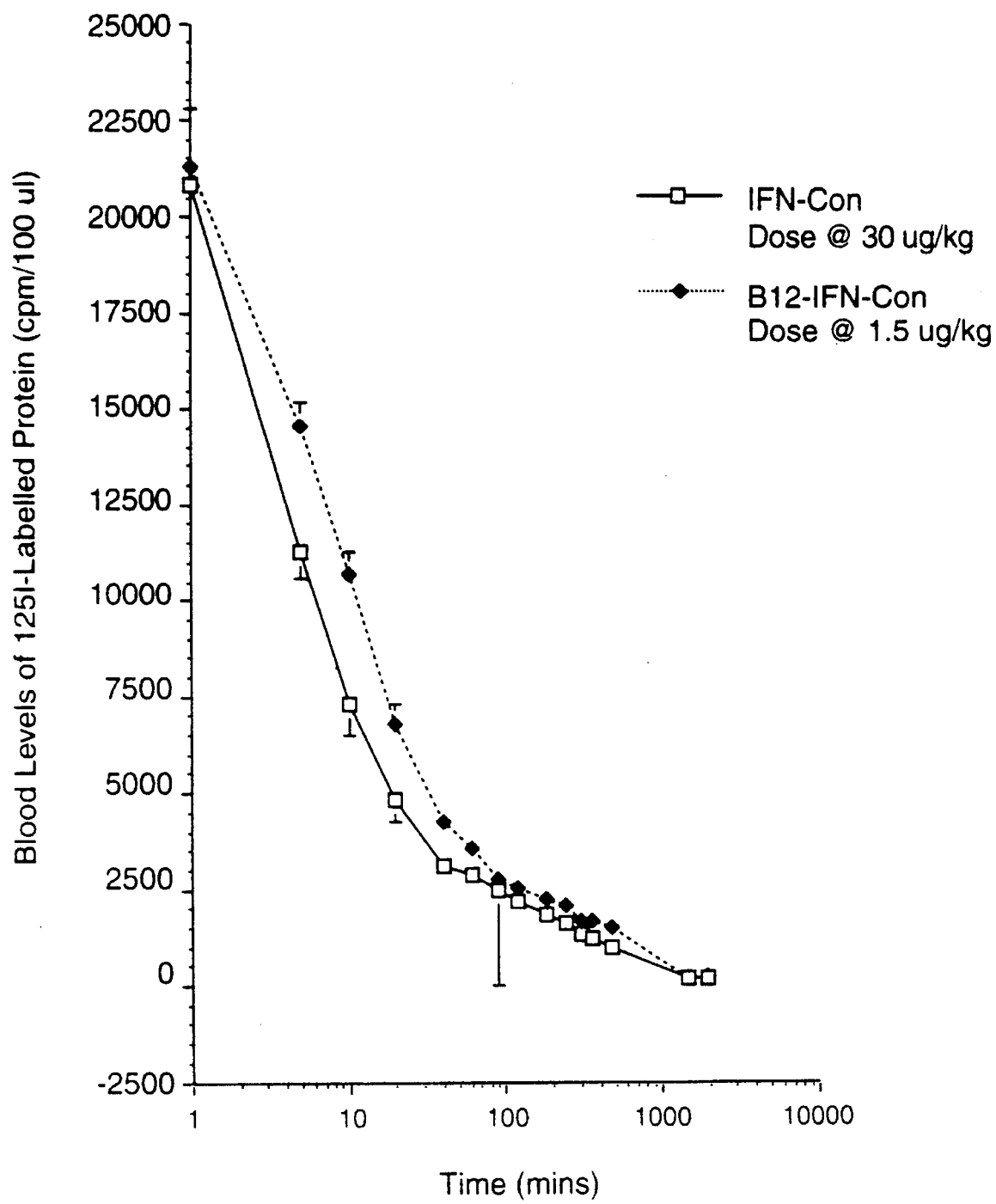
FIG. 11 is graphical representation of the blood levels, in counts per minute (cpm) per 100 microliters, of $^{125}$I-labelled IFN-Con as compared over time with an $^{125}$I-labelled conjugate of $VB_{12}$ and IFN-Con, following intravenous administration in rats.

The results of the pharmacokinetics study, which are depicted in FIG. 11, reveal that there is very little difference between the behavior of native IFN-Con and $VB_{12}$-IFN-Con conjugate in the circulating blood of the two test groups of rats at the doses shown. While blood levels of the conjugate appear to be cleared slower than for IFN-Con alone, both materials were cleared from the circulation within about an hour after administration.

Figure 12A:
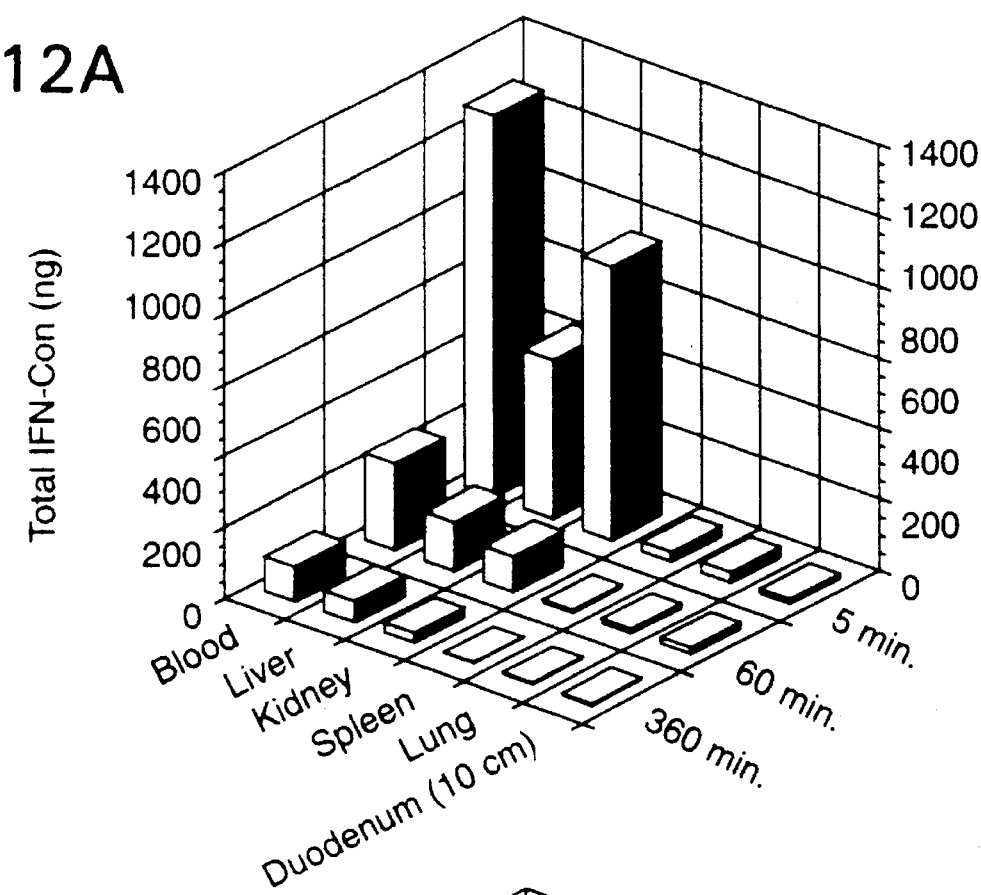
FIG. 12 shows the biodistribution of native IFN-Con (panel A) compared with a conjugate of IFN-Con with $VB_{12}$ (panel B), in total nanograms per organ, following intravenous administration to the rat. Three time points, five minutes, sixty minutes and six hours, were used.
Figure 12B:
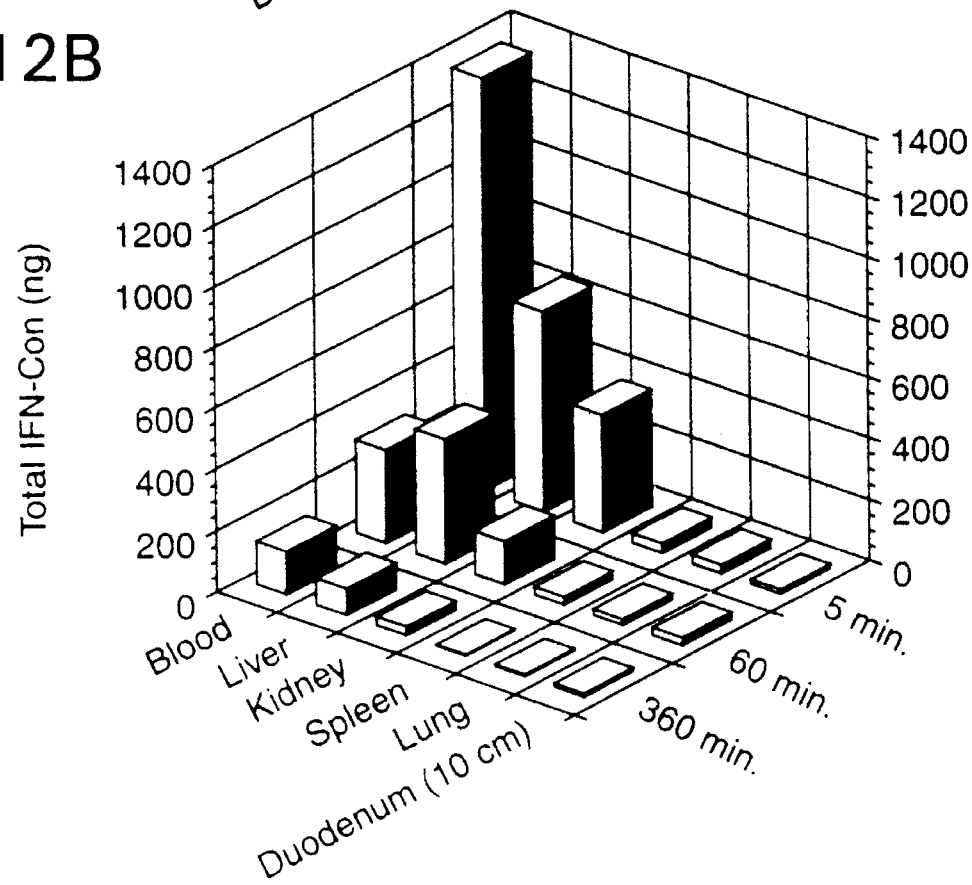
Figure 13:
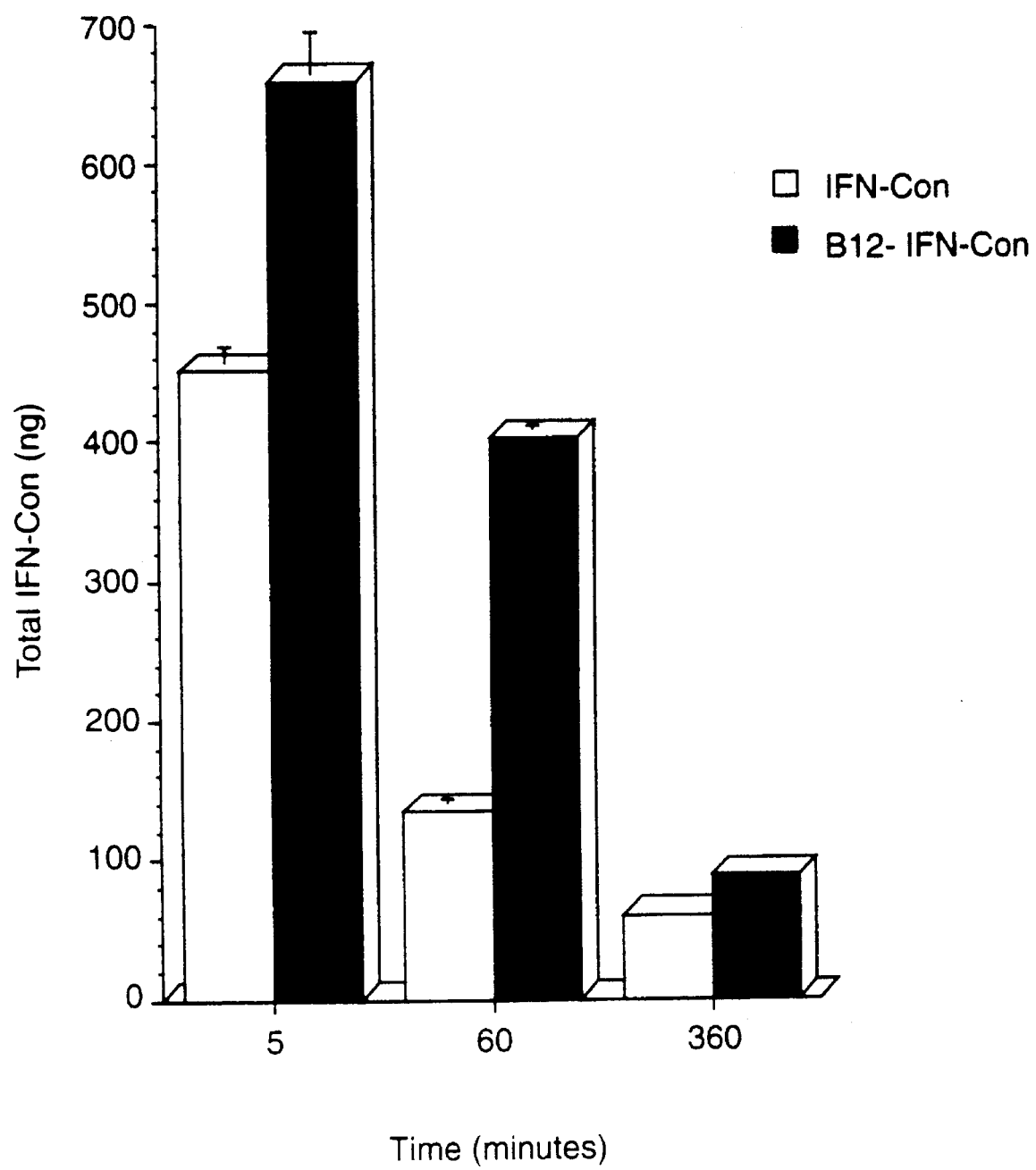
FIG. 13 shows the amount of native IFN-Con as compared with $VB_{12}$-IFN-Con conjugate, in total nanograms, in the liver of rats (n=4), following intravenous administration. The same three time points of FIG. 12 are shown.

The results of the biodistribution study (FIGS. 12 and 13) are especially interesting. As with the pharmacokinetics study there was very little difference in the circulating levels between native IFN-Con (FIG. 12, panel A) and $VB_{12}$-IFN-Con conjugate (FIG. 12, panel B). Distribution to the liver and kidney was most affected by the presence of the $VB_{12}$ on the protein. The liver, especially, had clearly elevated levels of the conjugate compared to native IFN-Con, with a 1.5-fold increase after only five minutes. The increase was even more pronounced one hour after administration (a three-fold increase). After six hours, there was no difference (FIG. 12 and FIG. 13).

The distribution of the native IFN-Con and the conjugated IFN-Con in the kidney (FIG. 12) was found to be just the opposite. The major route of elimination of INF-Con from the body is by glomerular filtration, and it would appear that this process is hindered by the presence of $VB_{12}$. This phenomenon might also explain why the circulating levels of conjugate were generally higher than for native IFN-Con in this study.

These results have significant implications in terms of the utility of $VB_{12}$-IFN-Con conjugate in treating viral infections such as hepatitis, which typically affect the liver. Due to the increased delivery of the conjugate to the liver, almost three-fold in this study, the conjugate may prove to be a more effective therapeutic by increasing the efficacy of IFN-Con at that organ. This potential is especially important for an orally delivered $VB_{12}$-IFN-Con conjugate. First pass metabolism dictates that all absorption from the gut first goes through the liver before being distributed through the body. It appears that $VB_{12}$ may help to prevent such distribution and target the orally delivered conjugate to the liver. This effect would be especially important with a therapeutic designed to treat hepatitis.

We claim:

1. A biologically active conjugate of vitamin $B_{12}$ and a therapeutic protein in which the therapeutic protein is covalently linked to a dicarboxylic acid derivative of the primary (5') hydroxyl group of the ribose moiety of vitamin B12.

2. A biologically active conjugate of vitamin $B_{12}$ and a therapeutic protein according to claim 1, which has the formula:

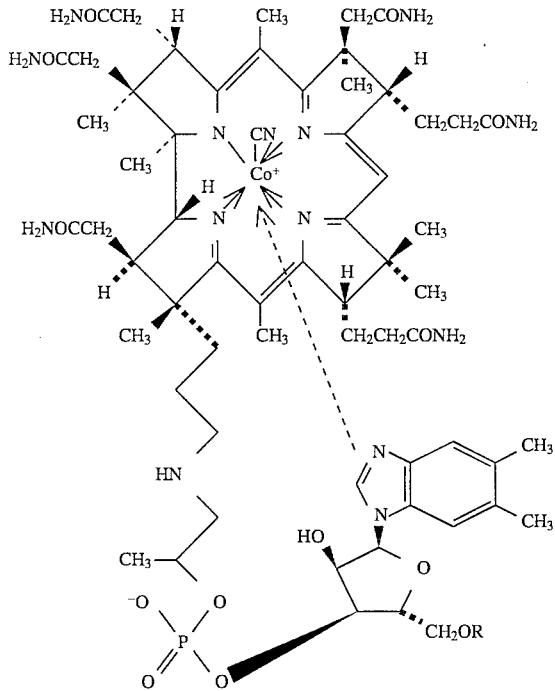

in which R is (1) $CO-(CH_2)_n-COR_1$ wherein $R_1$ is the protein, or (2) $CO-(CH_2)_n-CONH-(CH_2)_{12}-NHCOCH_2CH_2-S-R_3$ wherein $R_3$ is the protein, or (3) $CO-(CH_2)_n-CONH-(CH_2)_7COR_1$ wherein $R_1$ is the protein, or (4) $CO-(CH_2)_n-CONHNHCO(CH_2)_4$ $CONHNHR_1$ wherein $R_1$ is the protein, or (5) $CO-(CH_2)_n-CONHNHCO(CH_2)_4CONHN=R_4$ wherein $R_4$ is the protein, and n is an integer from 1 to 12.

3. A biologically active conjugate of vitamin $B_{12}$ and a therapeutic protein according to claim 1, in which the therapeutic protein is erythropoietin.

4. A biologically active conjugate of vitamin $B_{12}$ and a therapeutic protein according to claim 1, in which the therapeutic protein is granulocyte colony stimulating factor.

5. A biologically active conjugate of vitamin $B_{12}$ and a therapeutic protein according to claim 1, in which the therapeutic protein is consensus interferon.

6. A biologically active conjugate of vitamin B12 and a therapeutic protein according to claims 3, 4, or 5 in which the therapeutic protein is made by recombinant means.

7. A pharmaceutical composition comprising a biologically active conjugate of vitamin $B_{12}$ and a therapeutic protein according to claim 1 and a pharmaceutically acceptable carrier.

8. A pharmaceutical composition according to claim 7 which is capable of undergoing uptake in and transport through the gut of a mammal to deliver biologically active amounts of the therapeutic protein in the bloodstream.

9. A method for preparing a biologically active conjugate of vitamin B12 and a therapeutic protein according to claims 1 or 2, comprising the steps of:

a) forming a chemically reactive derivative of vitamin B12 by appending to the primary (5') hydroxyl group on the ribose moiety a chemically reactive carboxyl group;

b) optionally converting the chemically reactive carboxyl group on the ribose moiety into a mixed acid anhydride, acid halide, or activated ester functional group which is capable of being covalently linked to a therapeutic protein;

c) reacting the vitamin B12 derivative of step (a) or step (b) with the therapeutic protein to form a biologically active conjugate of vitamin B12 and the therapeutic protein; and d) recovering the conjugate.

10. A method according to claim 9, in which in step (a) a 5'-O-glutaroyl derivative of vitamin B12 is formed which is capable of further chemical modification.

11. A method according to claim 10, in which step (b) is carried out to convert the 5'-O-glutaroyl derivative of vitamin $B_{12}$ from step (a) into an acylating agent.

12. A method according to claim 11 in which the 5'-O-glutaroyl derivative of vitamin B12 is converted into a mixed acid anhydride, an acid halide, or an activated ester.

13. A method according to claim 12 in which the active ester is the N-hydroxysuccinimidyl active ester.

14. A method according to claim 9 in which step (c) is carried out in the presence of a carboxyl group activating agent.

15. A pharmaceutical composition comprising (1) a biologically active conjugate of vitamin B12 and a therapeutic protein in which the therapeutic protein is covalently linked to a dicarboxylic acid derivative of the primary (5') hydroxyl group of the ribose moiety of vitamin B12;

(2) an absorption enhancing amount of human intrinsic factor; and (3) optionally, a pharmaceutically acceptable carrier.

16. A pharmaceutical composition according to claim 15 in which the biologically active conjugate of vitamin $B_{12}$ and therapeutic protein has the formula:

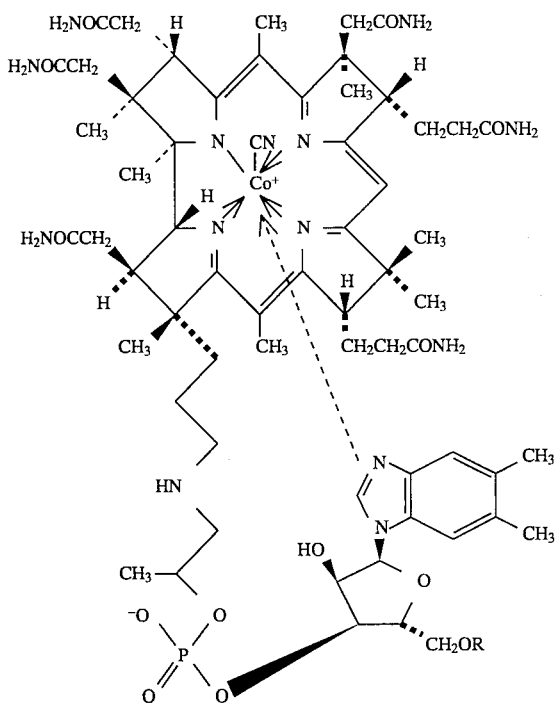

in which R is

1) CO—(CH$_2$)$_n$—COR$_1$ wherein R$_1$ is the protein, or
2) CO—(CH$_2$)$_n$—CONH—(CH$_2$)$_{12}$—NHCOCH$_2$CH$_2$—S—R$_3$ wherein R$_3$ is the protein, or
3) CO—(CH$_2$)$_n$—CONH—(CH$_2$)$_7$COR$_1$ wherein R$_1$ is the protein, or
(4) CO—(CH$_2$)$_n$—CONHNHCO(CH$_2$)$_4$ CONHNHR$_1$ wherein R$_1$ is the protein, or
(5) CO—(CH$_2$)$_n$—CONHNHCO(CH$_2$)$_4$ CONHN=R$_4$ wherein R$_4$ is the protein, and n is an integer from 1 to 12.

17. A pharmaceutical composition according to claim 15 in which the therapeutic protein is selected from the group consisting of erythropoietin, granulocyte colony stimulating factor and consensus interferon.

18. A method for enhancing the absorption in a mammal of an orally administered therapeutic protein, comprising administering the protein in the form of a conjugate according to claims 1 or 2.

19. A method according to claim 18 in which the conjugate is administered with intrinsic factor.

20. A method according to claims 18 or 19 in which the mammal is a human being.

21. A method for delivering a therapeutic protein to the liver via oral administration, comprising using a biologically active conjugate of vitamin B12 and a therapeutic protein according to claims 1 or 2.

22. A method according to claim 21 in which the therapeutic protein is consensus interferon.

23. A method according to claims 21 or 22 which involves in vivo administration to a human being.

24. A method for preparing a biologically active conjugate of vitamin B12 and a therapeutic protein, comprising:
   a) forming a 5'-O derivative of a vitamin B12 compound, wherein the derivative is capable of being covalently linked to a therapeutic protein; and
   b) reacting the 5'-O derivative from step (a) with the therapeutic protein to form the biologically active conjugate.

* * * * *